United States Patent
Isobe et al.

(10) Patent No.: US 8,739,643 B2
(45) Date of Patent: Jun. 3, 2014

(54) REMOTE-CONTROLLED ACTUATOR

(75) Inventors: Hiroshi Isobe, Iwata (JP); Yoshitaka Nagano, Iwata (JP); Yukihiro Nishio, Iwata (JP)

(73) Assignee: NTN Corporation, Osaka (JP)

( * ) Notice: Subject to any disclaimer, the term of this patent is extended or adjusted under 35 U.S.C. 154(b) by 265 days.

(21) Appl. No.: 13/394,003

(22) PCT Filed: Sep. 22, 2010

(86) PCT No.: PCT/JP2010/066386
§ 371 (c)(1), (2), (4) Date: Mar. 2, 2012

(87) PCT Pub. No.: WO2011/037130
PCT Pub. Date: Mar. 31, 2011

(65) Prior Publication Data
US 2012/0152045 A1    Jun. 21, 2012

(30) Foreign Application Priority Data

Sep. 28, 2009   (JP) ................................. 2009-222303

(51) Int. Cl.
*A61B 17/32*   (2006.01)
(52) U.S. Cl.
USPC ............. 74/22 R; 606/180; 606/170; 606/171
(58) Field of Classification Search
USPC ...... 74/22 R, 424.81, 424.93, 22 A; 600/180, 600/80, 170, 171; 175/61, 75
See application file for complete search history.

(56) References Cited

U.S. PATENT DOCUMENTS

| 4,057,115 | A | * | 11/1977 | Blanz ............................. 173/160 |
| 4,124,026 | A | * | 11/1978 | Berner et al. .................. 606/104 |
| 4,265,231 | A |   | 5/1981 | Scheller, Jr. et al. |
| 4,466,429 | A |   | 8/1984 | Loscher et al. |
| 5,084,052 | A | * | 1/1992 | Jacobs ............................. 606/79 |
| 5,269,785 | A | * | 12/1993 | Bonutti ........................... 606/80 |

(Continued)

FOREIGN PATENT DOCUMENTS

| JP | 10-296671 | 11/1998 |
| JP | 2001-17446 | 1/2001 |

(Continued)

OTHER PUBLICATIONS

International Search Report for PCT/JP2010/066386 mailed Nov. 16, 2010.

(Continued)

*Primary Examiner* — David M Fenstermacher

(57) ABSTRACT

A remote control actuator includes a spindle guide section (3), a distal end member (2) fitted to the tip of the spindle guide section for alteration in attitude, a tool (1) provided rotatably in the distal end member, a tool rotation drive source (41) for rotating the tool, and an attitude altering drive source (42) for altering the attitude of the distal end member. The spindle guide section has therein a rotary shaft (22) for transmitting a rotation of the tool rotation drive source to the tool, and an attitude altering member (31) capable of being selectively advanced or retracted by the attitude altering drive source for altering the attitude of the distal end member. A position detector (47) is provided for detecting the advanced or retracted position of the attitude altering member at a site distant from the attitude altering drive source.

11 Claims, 14 Drawing Sheets

(56) References Cited

U.S. PATENT DOCUMENTS

| | | | |
|---|---|---|---|
| 6,312,438 B1 * | 11/2001 | Adams | 606/159 |
| RE38,018 E * | 3/2003 | Anctil et al. | 606/170 |
| 6,591,698 B1 | 7/2003 | Carlsson et al. | |
| 8,128,633 B2 * | 3/2012 | Linderman et al. | 606/94 |
| 8,262,683 B2 * | 9/2012 | McFarlin et al. | 606/170 |
| 8,511,195 B2 * | 8/2013 | Isobe et al. | 74/490.01 |
| 8,518,065 B2 * | 8/2013 | Shores et al. | 606/167 |
| 8,556,734 B2 * | 10/2013 | Isobe et al. | 464/23 |
| 8,568,415 B2 * | 10/2013 | Brunnett et al. | 606/79 |
| 8,573,090 B2 * | 11/2013 | Isobe et al. | 74/490.04 |
| 8,585,727 B2 * | 11/2013 | Polo | 606/170 |
| 8,597,299 B2 * | 12/2013 | Farr et al. | 606/86 A |
| 8,622,886 B2 * | 1/2014 | Young et al. | 600/30 |
| 8,623,266 B2 * | 1/2014 | Adams | 264/521 |
| 2005/0177168 A1 | 8/2005 | Brunnett et al. | |
| 2007/0265653 A1 | 11/2007 | Suzuki | |
| 2009/0143642 A1 | 6/2009 | Takahashi et al. | |

FOREIGN PATENT DOCUMENTS

| | | |
|---|---|---|
| JP | 2001-507587 | 6/2001 |
| JP | 2007-521916 | 8/2007 |
| JP | 2007-301149 | 11/2007 |
| JP | 2009-131374 | 6/2009 |
| WO | WO 98/27886 | 7/1998 |
| WO | WO 2005/077284 A2 | 8/2005 |

OTHER PUBLICATIONS

International Preliminary Report on Patentability mailed Apr. 19, 2012 issued in corresponding International Patent Application No. PCT/JP2010/066386.

Japanese Office Action mailed Oct. 22, 2013 in corresponding Japanese Application No. 2009-222303.

* cited by examiner

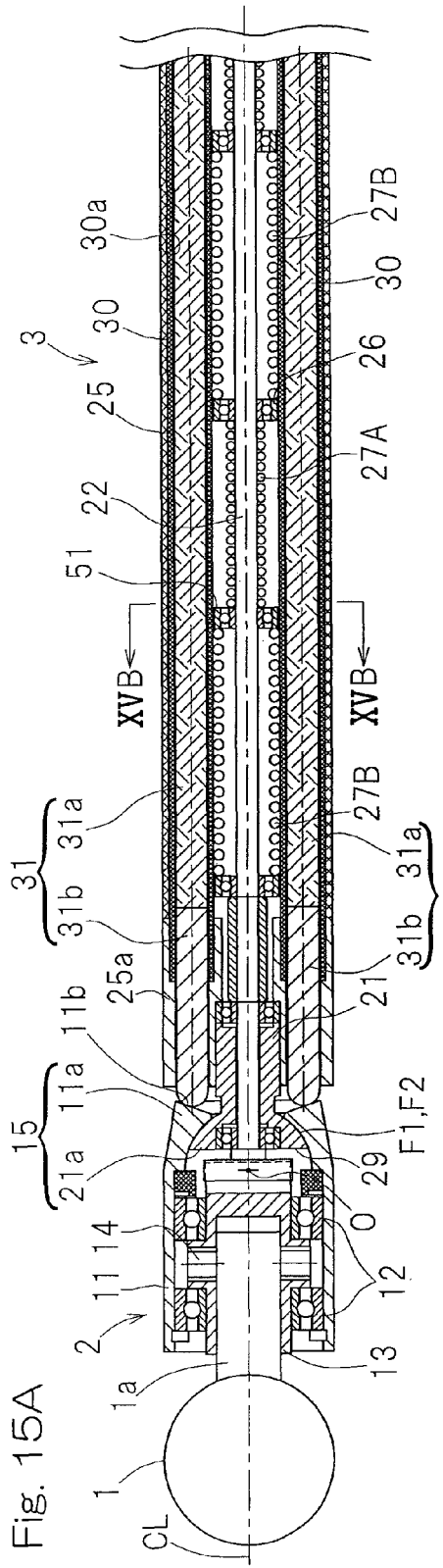
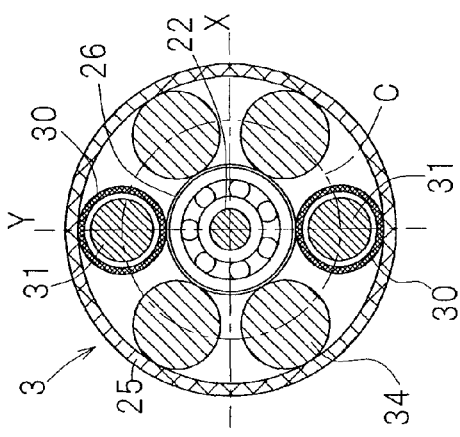
Fig. 15A
Fig. 15B

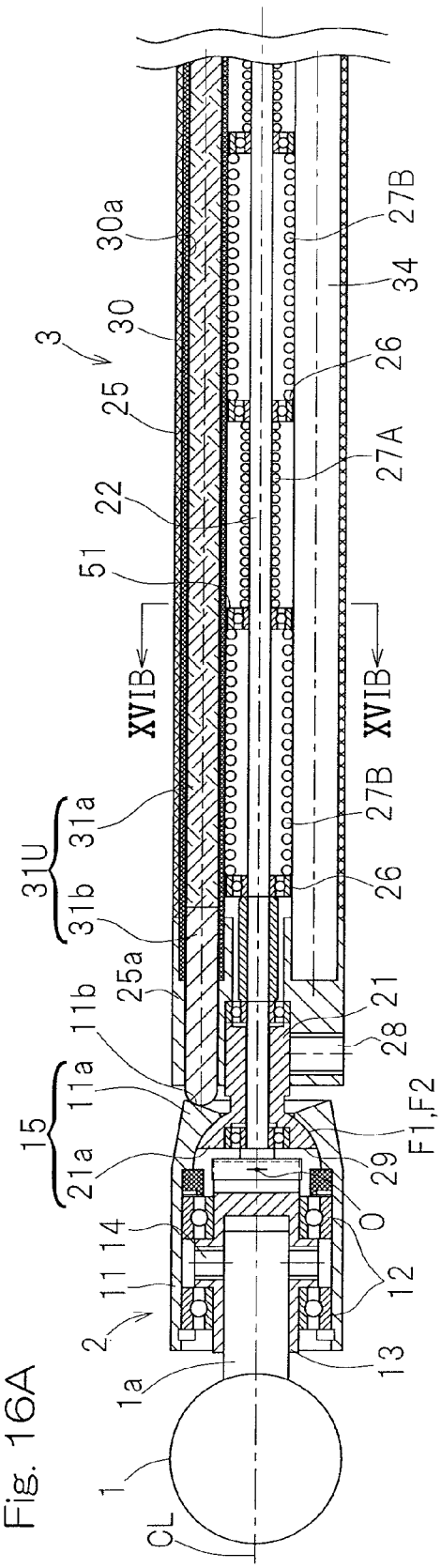
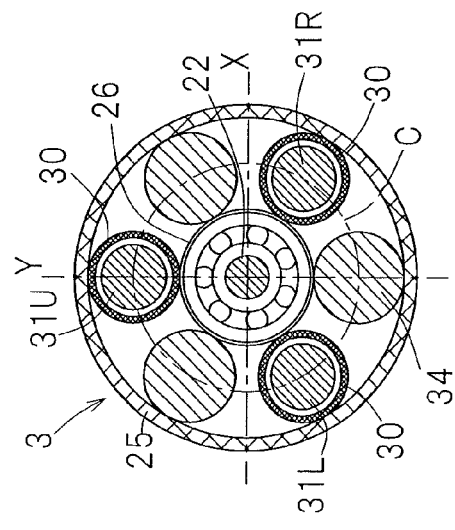
Fig. 16A
Fig. 16B

REMOTE-CONTROLLED ACTUATOR

CROSS REFERENCE TO RELATED APPLICATIONS

This application claims the benefit under 35 U.S.C. Section 371, of PCT International Application No. PCT/JP2010/066386, filed Sep. 22, 2010, which claimed priority to Japanese Application No. 2009-222303, filed Sep. 28, 2009 in the Japanese Patent Office, the disclosures of which are hereby incorporated by reference.

BACKGROUND OF THE INVENTION

1. Field of the Invention

The present invention relates to a remote controlled actuator for use in medical and machine processing fields and capable of changing the attitude of a machine tool.

2. Description of Related Art

Remote controlled actuators are currently available; some are used in the medical field for osteal treatment and some are used in the mechanical processing field for drilling and cutting. Any of those remote controlled actuators controls by remote control a machine tool fitted to a distal end of an elongated pipe of a linear or curved configuration. However, since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip joint replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet this desire, the following technique has hitherto been suggested. For example, the Patent Document 2 listed below discloses the elongated pipe having its intermediate portion curved twice to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated by 180°.

Prior Art Literature

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] JP Laid-open Patent Publication No. 2001-17446

If in a condition, in which the artificial joint is inserted into an artificial joint insertion hole formed in the living bone, a large gap exists between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever shape the pipe takes, the working range of the tool is limited by the shape of the pipe and, therefore, it is difficult to process the artificial joint insertion hole so that the living bone and the artificial joint may have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant or assignee of the present invention has attempted to provide a remote controlled actuator of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe. It has, however, been found that since the tool is connected to the distal end of the elongated pipe, disposition of a mechanism for changing the attitude of the tool is considerably limited and, therefore, artifices are required to overcome those limitations.

It is to be noted that in the case of the medical actuator having no elongated pipe used therein, a portion where the tool is mounted can change its attitude relative to a portion to be gripped by hand (See, for example, Patent Document 4 listed above), but nothing has yet been suggested in the art that the attitude of the tool can be altered by remote control.

SUMMARY OF THE INVENTION

An object of the present invention is to provide a remote control actuator of a type having a high accuracy in attitude alteration, in which the attitude of the tool coupled to the tip of the elongated pipe section can be changed by remote control and in which a spindle guide section as the pipe section can be altered in its attitude even if in a curved condition.

The remote controlled actuator of the present invention includes a spindle guide section of an elongated shape, a distal end member fitted to a tip of the spindle guide section through a distal end member connecting unit for alteration in attitude, a tool rotatably provided in the distal end member, a tool rotation drive source for rotating the tool, an attitude altering drive source for operating the attitude of the distal end member, and a drive unit housing to which a base end of the spindle guide section is connected. In such case, the distal end member rotatably supports a spindle for holding the tool and the spindle guide section has its interior accommodating a rotary shaft for transmitting a rotation of the tool rotation drive source to the spindle and a guide hole having its opposite ends opening. In such case, a flexible attitude altering member is reciprocally movably inserted within the guide hole and has a tip for undergoing a reciprocating or retracting motion in contact with the distal end member so as to alter the attitude of the distal end member, with the attitude altering member being selectively advanced or retracted by the attitude altering drive source. The remote controlled actuator further includes a position detector for detecting an advanced or retracted position of the attitude altering member from a site separate from the attitude altering drive source. For example, the position detector detects the advanced or retracted position of the attitude altering member from the displacement of the attitude altering member or a force transmitting member between the attitude altering drive source and the attitude altering member.

According to the above described construction, as a result of rotation of the tool fitted to the distal end member, cutting of the bone or the like takes place. In such case, when the attitude altering member is selectively advanced and retracted one at a time by the attitude altering drive source, the tip end of the attitude altering member works on the distal end member to allow the attitude of the distal end member, fitted to the tip end of the spindle guide section through the distal end member connecting unit for alteration in attitude, to alter. The attitude altering drive source is provided at a position distant from the distal end member and the alteration of the attitude of the distal end member is carried out by remote control. Since the attitude altering member is passed through the guide hole, the attitude altering member can work on the distal end member properly at all time without being displaced in a direction transverse to the longitudinal direction thereof, and the operation to alter the attitude of the distal end member takes place accurately. Also, since the attitude altering member is flexible, the attitude altering operation takes place assuredly even when the spindle guide section is of a type having a curved portion.

The attitude of the distal end member can be estimated from the advanced or retracted position of the attitude altering member detected by the position detector. If the attitude of the distal end member is ascertained, the tip position of the tool is also ascertained and as a result, the processing with the tool can be accomplished accurately. Since the position detector is provided at a site separate from the attitude altering drive source, for example, the attitude altering member or the force transmitting member between the attitude altering drive source and the attitude altering member so that the advanced or retracted position of the attitude altering member can be detected at a position near to the attitude altering member, the detecting accuracy is high. By way of example, where the advanced or retracted position of the attitude altering member is to be estimated from the amount of activation of the attitude altering drive source, deformation or rattling motion of the force transmitting member between the attitude altering drive source and the attitude altering member appears as an error. However, detection at the position near to the attitude altering member is effective to increase the detecting accuracy with the error minimized.

In the present invention, the use may be made of a force increasing and transmitting mechanism within the drive unit housing, which mechanism is comprised of a lever mechanism for increasing and transmitting to the attitude altering member, an output of a direct acting member, which is selectively advanced or retracted by the attitude altering drive source in a linear direction. In such case, with a lever of the force increasing and transmitting mechanism used as the transmitting member, the position detector may include a displacement amount measuring unit for measuring the amount of displacement of the lever and a displacement amount estimator for estimating the advanced or retracted position of the attitude altering member from a measured value of the displacement amount measuring unit. The use of the force increasing and transmitting mechanism is effective to increase an output of the attitude altering drive source and, therefore, the attitude altering drive source can be made compact. In case of use of the force increasing and transmitting mechanism, if the position detector is of a structure including the displacement amount measuring unit and the displacement amount estimator, the amount of displacement of the lever of the force increasing and transmitting mechanism, which is the force transmitting member between the attitude altering drive source and the attitude altering member, is measured by the displacement amount measuring unit and, from the measured value thereof, the displacement amount estimator can estimate the advanced or retracted position of the attitude altering member.

For example, the displacement amount measuring unit may be a displacement sensor having a to-be-detected portion, provided in the lever of the force increasing and transmitting mechanism, and a detecting portion fixed in position to the drive unit housing for detecting a displacement of the to-be-detected portion. By detecting the displacement of the to-be-detected portion provided in the lever of the force increasing and transmitting with the detecting portion, the angle of rotation of the lever can be estimated. Once the angle of rotation of the lever is ascertained, the advanced or retracted position of the attitude altering member can be determined.

Alternatively, the displacement amount measuring unit may be an angle sensor for detecting the angle of rotation of the lever of the force increasing and transmitting mechanism. Even if the angle of rotation of the lever of the force increasing and transmitting mechanism is detected with such an angle sensor, the advanced or retracted position of the attitude altering member can be determined.

In the present invention, the position detector may include an advanced or retracted position measuring unit for measuring the advanced or retracted position of one end of the attitude altering member adjacent the drive unit housing, and an advanced or retracted position estimator for estimating the advanced or retracted position of the attitude altering member from a measured value of the advanced or retracted position measuring unit. According to this construction, the advanced or retracted position of one end of the attitude altering member adjacent the drive unit housing is measured with the advanced or retracted position measuring unit and, from the measured value thereof, the displacement amount estimator estimates the advanced or retracted position of the attitude altering member. Since the advanced or retracted position measuring unit detects directly the advanced or retracted position of that end of the attitude altering member, deformation or rattling motion of the force transmitting member between the attitude altering drive source and the attitude altering member does not appear as an error and therefore, the detecting accuracy is high.

By way of example, the advanced or retracted position measuring unit may include a to-be-detected portion, provided at one end of the attitude altering member adjacent the drive unit housing and made up of a flat face lying perpendicular to a lengthwise direction of the attitude altering member, and a detecting portion fixed in position to the drive unit housing for detecting a displacement of the to-be-detected portion. If the displacement of the to-be-detected portion provided in the attitude altering member is detected by the detecting portion fixed in position, the advanced or retracted position of the attitude altering member can be determined.

Alternatively, the advanced or retracted position measuring unit may include a to-be-detected portion in the form of a linear encoder, provided at one end of the attitude altering member adjacent the drive unit housing and having scale grids to be detected lined up on a lengthwise direction of the attitude altering member, and a detecting portion fixed in position to the drive unit housing for reading the scale grids of the to-be-detected portion. If the scale grids of the to-be-detected portion comprised of the linear encoder provided in the attitude altering member are read by the detecting portion fixed in position, the advanced or retracted position of the attitude altering member can be detected.

In the present invention, the attitude altering drive source is a rotary actuator provided outside the drive unit housing, in which case the use may be made of a rotation/advance or retraction converting and transmitting mechanism that is accommodated within the drive unit housing and is operable to convert the rotation of the attitude altering drive source into the advancing or retracting motion in the linear direction and then to transmit it to the attitude altering member. If the attitude altering drive source is employed in the form of the rotary actuator, even in case of the provision of the attitude altering drive source at a location outside the drive unit housing, the rotation of the attitude altering drive source can easily be transmitted to the rotation/advance or retraction converting and transmitting mechanism. If the attitude altering drive source is provided outside the drive unit housing, the drive unit housing can be made compact. For this reason, the handleability at the time the remote controlled actuator is operated with the drive unit housing carried by an operator can be increased.

In the present invention, the use may be made of an activation amount measuring unit for measuring the amount of activation of the attitude altering drive source and an applied force estimator for estimating the magnitude of a force, which the attitude altering member applies to the distal end member, from a difference between the advanced or retracted position of the attitude altering member, that is estimated from the amount of activation of the attitude altering drive source measured by the activation amount measuring unit, and the advanced or retracted position of the attitude altering member estimated from the position detector. Deformation and rattling motion of the force transmitting member between the attitude altering drive source and the attitude altering member change with a change of the magnitude of the force the force transmitting member applies to the attitude altering member. More specifically, if the force applied to the attitude altering member increases, the deformation of the force transmitting member also increases. In other words, the larger the force applied to the attitude altering member, the larger the difference between the advanced or retracted position of the attitude altering member, which is estimated from the amount of activation of the attitude altering drive source, and the advanced or retracted position of the attitude altering member, which is estimated by the position detector. The magnitude of the force applied to the attitude altering member by the force transmitting member is nothing other than the magnitude of the force the attitude altering member applies to the distal end member. Accordingly, from the magnitude of the difference of the above discussed retracted or advanced positions, the magnitude of the force applied to the distal end member by the attitude altering member can be estimated.

In the present invention, the spindle guide section has a curved portion. Since the attitude altering member is flexible, it can be selectively advanced or retracted within the guide hole even though the spindle guide section is of a shape having a curved portion.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 15A is a longitudinal sectional view showing the distal end member and the spindle guide section, both employed in the remote controlled actuator designed in accordance with a ninth preferred embodiment of the present invention, in which a different mechanism for altering the attitude of the distal end member is employed;

FIG. 15B is a cross sectional view taken along the line XVB-XVB in FIG. 15A;

FIG. 16A is a longitudinal sectional view showing the distal end member and the spindle guide section, both employed in the remote controlled actuator designed in accordance with a tenth preferred embodiment of the present invention, in which another different mechanism for altering the attitude of the distal end member is employed;

FIG. 16B is a cross sectional view taken along the line XVIB-XVIB in FIG. 16A;

DESCRIPTION OF PREFERRED EMBODIMENTS

Figure 1:
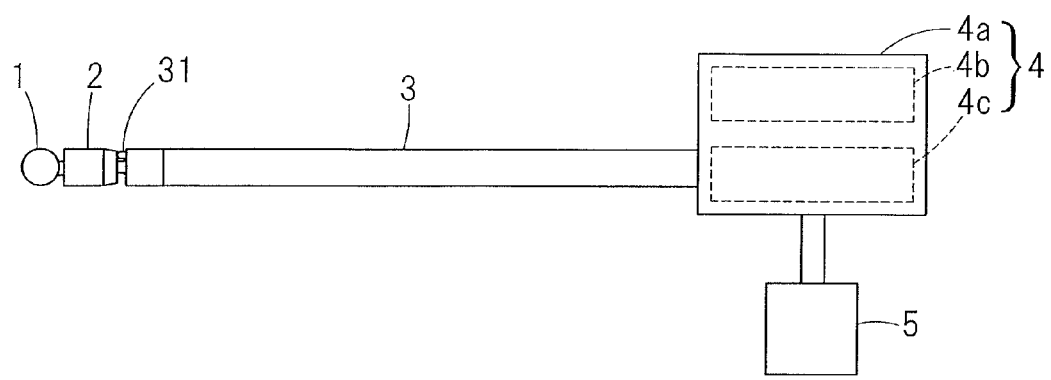
FIG. 1 is a diagram showing a schematic structure of a remote controlled actuator designed in accordance with a first preferred embodiment of the present invention.
Figure 2:
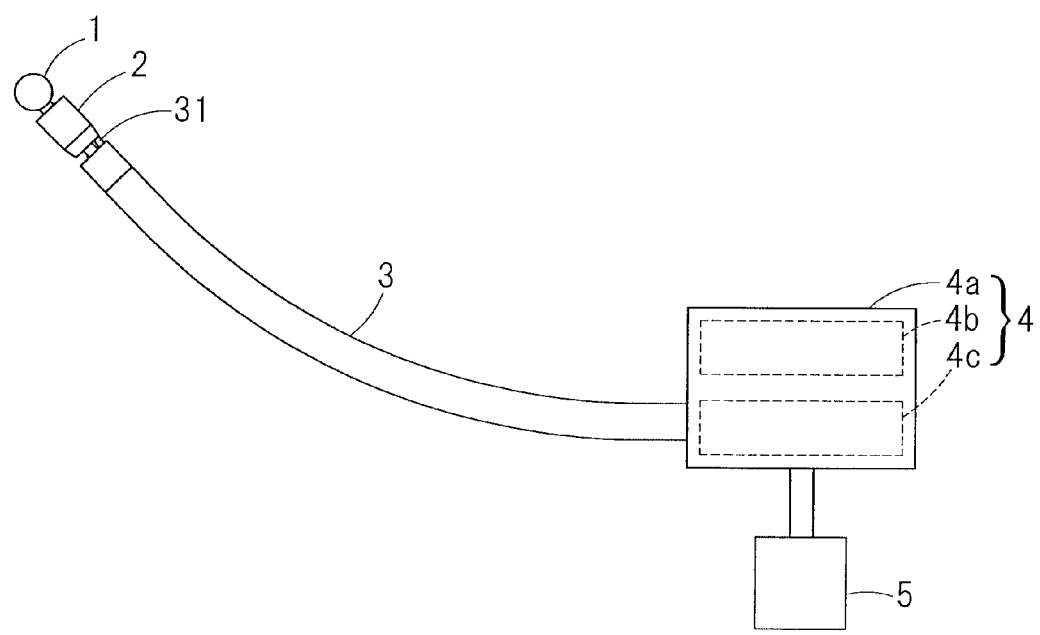
FIG. 2 is a diagram showing a schematic structure of a remote controlled actuator designed in accordance with a second preferred embodiment of the present invention.

FIGS. 1 and 2 illustrate schematic structures of remote controlled actuators designed in accordance with first and second preferred embodiments of the present invention, respectively. Each of those remote controlled actuators includes a distal end member 2 for holding a rotary tool 1, a spindle guide section 3 of an elongated shape having a tip to which the distal end member 2 is fitted for alteration in attitude, a drive unit housing 4a to which a base end of the spindle guide section 3 is connected, and a controller 5 for controlling a tool rotation drive mechanism 4b and an attitude altering drive mechanism 4c, both accommodated within the drive unit housing 4a. The drive unit housing 4a forms a drive unit 4 together with the built-in tool rotation drive mechanism 4b and the similarly built-in attitude altering drive mechanism 4c.

Figure 3A:
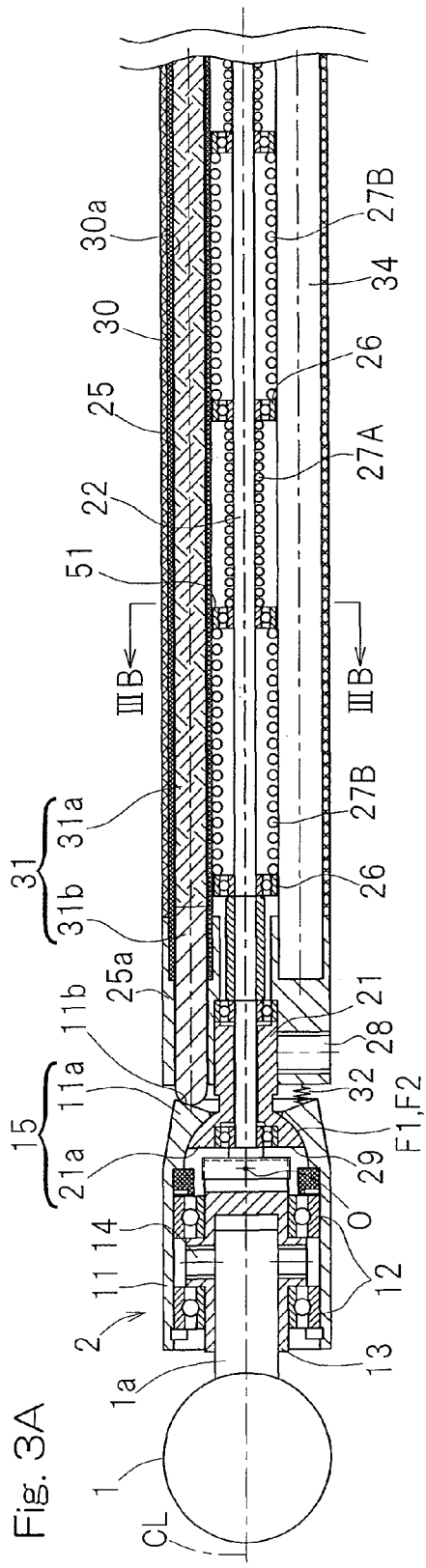
FIG. 3A is a longitudinal sectional view showing a distal end member and a spindle guide section both employed in the remote controlled actuator according to the first embodiment of FIG. 1.
Figure 3C:
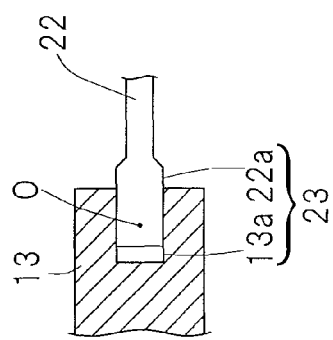
FIG. 3C is a diagram showing a connecting structure between the distal end member and a rotary shaft.
Figure 3B:
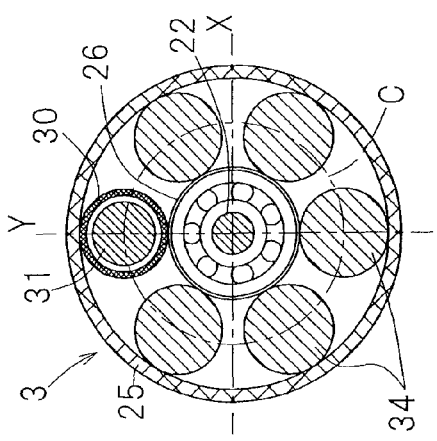
FIG. 3B is a cross sectional view taken along the line IIIB-IIIB in FIG. 3A.

An internal structure of each of the distal end member 2 and the spindle guide section 3 will be described in detail with particular references to FIGS. 3A to 3C. It is to be noted that although FIGS. 3A to 3C illustrate the remote controlled actuator of the type shown in FIG. 1, the respective internal structures of the distal end member 2 and the spindle guide section 3 remain basically the same regardless of whether the spindle guide section 3 is of a linear shape as shown in FIG. 1 or whether the spindle guide section 3 is of a curved shape as shown in FIG. 2.

The distal end member 2 includes a generally or substantially cylindrical housing 11 and a spindle 13 rotatably accommodated within such cylindrical housing 11 through a pair of bearings 12. The spindle 13 is of a tubular shape having a distal side opening and has a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member coupling unit 15. The distal end member coupling unit 15 supports the distal end member 2 for displacement in attitude and is comprised of a spherical bearing. More specifically, the distal end member coupling unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered. In the instance as shown, since the construction is so employed that the distal end member 2 can alter its attitude about an X-axis passing through the center O of curvature, the guide faces F1 and F2 may be cylindrical surface each having its longitudinal axis represented by the X-axis passing through the center O of curvature.

The spindle guide section 3 includes a rotary shaft 22 for transmitting a rotational force exerted by a tool rotating drive source 41 (FIG. 4A) accommodated within the drive unit housing 4a. In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 3C, the spindle 13 and the rotary shaft 22 are coupled together by means of a universal joint 23 for transmitting rotation from the rotary shaft 22 to the spindle 13. The universal joint 23 is made up of a groove 13a, defined in a closed base end of the spindle 13, and of a projection 22a defined in a distal end of the rotary shaft 22 and engageable in the groove 13a. The center of joint between the groove 13a and the projection 22a is located at the same position as the centers of curvature O of the guide faces F1 and F2.

The spindle guide section 3 has an outer shell pipe 25, which forms an outer shell of the spindle guide section 3, and the rotary shaft 22 referred to above is positioned at a center of this outer shell pipe 25. The rotary shaft 22 so positioned is rotatably supported by a plurality of rolling bearings 26 positioned spaced a distant apart from each other in a direction axially of the spindle guide section 3. Between the neighboring rolling bearings 26, spring elements 27A for generating a preload on the inner rings of the corresponding rolling bearing 26 and spring elements 27B for generating the preload on the outer rings of the corresponding rolling bearings 26 are alternately disposed relative to each other. Those spring elements 27A and 27B may be employed in the form of, for example, compression springs. The constraint member 21 referred to previously is fixed to a pipe end portion 25a of the outer shell pipe 25 by means of a fixing pin 28 and has its distal end inner peripheral portion supporting a distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

Provided between an inner diametric surface of the outer shell pipe 25 and the rotary shaft 22 is a guide pipe 30, having its opposite ends opening. Within a guide hole 30a which is an inner diametric hole of this guide pipe 30, an attitude altering or operating member 31 is reciprocally movably inserted. In the instance as shown, the attitude altering member 31 is in the form of a wire 31a and pillar shaped pins 31b connected to a tip end of the wire 31a. The attitude altering member 31 has a tip end representing a spherical shape which is held in contact with a bottom face of a radial groove portion 11b formed in a base (or proximal) end face of the housing 11. The other of the pillar shaped pins 31b that is closer to the drive unit housing 4a also has a tip end representing a spherical shape which is held in contact with a lateral surface of a pivot lever 43b (FIG. 4A) which will be explained in detail later.

Between a base end face of the housing 11 of the distal end member 2 and a tip end face of the outer shell pipe 25 of the spindle guide section 3, a restoring elastic member 32 made of, for example, a compression coil spring, is arranged at a location spaced 180° degrees circumferentially in phase from the circumferential location where the attitude altering member 31 is positioned. The restoring elastic member 32 biases the distal end member 2 towards a predetermined attitude.

Also, a plurality of reinforcement shafts 34 are arranged, separate from the guide pipe 30, between the inner diametric surface of the outer shell pipe 25 and the rotary shaft 22 and on the same pitch circle C as that depicted by the guide pipe 30. Those reinforcement shafts 34 are employed for securing the rigidity of the spindle guide section 3. The guide pipe 30 and the plural reinforcement shafts 34 are spaced an equal distance from each other. The guide pipe 30 and the plural reinforcement shafts 34 are held in contact with the inner diametric surface of the outer shell pipe 25 and an outer diametric surface of each of the rolling bearings 26 so as to support the respective outer diametric surfaces of the rolling bearings 26.

Figure 4A:
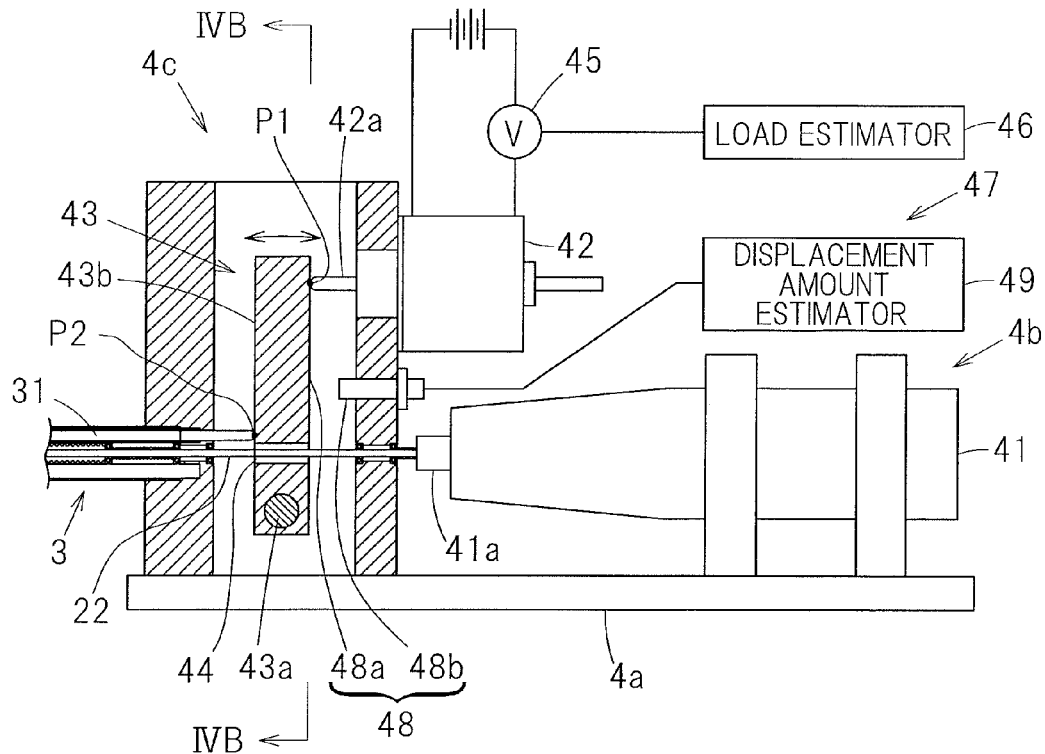
FIG. 4A is a diagram illustrating a partially sectional view of a tool rotation drive mechanism and an attitude altering drive mechanism, both employed in the remote controlled actuator, shown together with a control system.
Figure 4B:
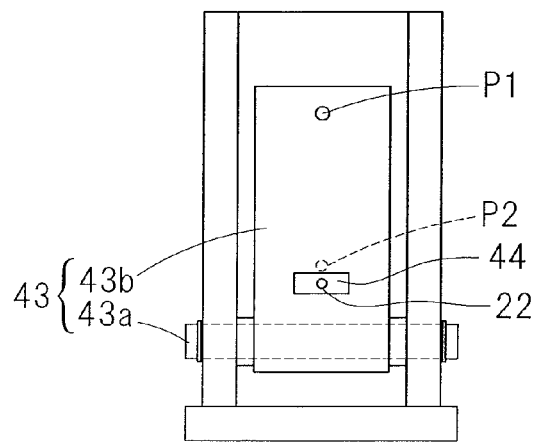
FIG. 4B is a cross sectional view taken along the line IVB-IVB in FIG. 4A.

FIGS. 4A and 4B illustrate the tool rotation drive mechanism 4b and the attitude altering drive mechanism 4c both accommodated within the drive unit housing 4a. The tool rotation drive mechanism 4b includes the tool rotation drive source 41 adapted to be controlled by the controller 5 (best shown in FIGS. 1 and 2). The tool rotation drive source 41 is in the form of, for example, an electrically driven motor having its output shaft 41a coupled with a base end of the rotary shaft 22. The attitude altering drive mechanism 4c includes an attitude altering drive source 42 adapted to be controlled by the controller 5 (best shown in FIGS. 1 and 2). This attitude altering dive source 42 is in the form of, for example, an electrically driven actuator, and the movement of an output rod 42a, which is a direct acting member capable of selectively advancing and retracting, i.e., reciprocally movable in a direction leftwards and rightwards as viewed in FIG. 4A, is transmitted to the attitude altering member 31 through a force increasing and transmitting mechanism 43.

The force increasing and transmitting mechanism 43 is comprised of a lever mechanism and includes a pivot lever 43b pivotable about a support pin 43a and is so designed and so configured as to allow a force of the output rods 42a to work on a working point P1 of the levers 43b, which are respectively spaced a long distance from the support pin 43a, and as to apply a force to the attitude altering members 31 at a force point P2, which are spaced a short distance from the support pin 43a, wherefore the outputs of the attitude altering drive sources 42 can be increased and then transmitted to the attitude altering members 31. Since the use of the force increasing and transmitting mechanism 43 is effective to enable a large force to be applied to the attitude altering members 31 even in the linear actuator of a low output capability, the linear actuator can be downsized. The rotary shaft 22 referred to above is made to extend through an opening 44 defined in the pivot lever 43b.

The attitude altering drive mechanism 4c is provided with a supply power meter 45 for detecting the electric energy supplied to the attitude altering drive source 42, which is an electrically operated actuator, independent of each other. The detection value of this supply power meter 45 is outputted to a load estimator 46. This load estimator 46 in turn detects a load acting on the distal end member 2 in reference to the outputs of the supply power meter 45. Specifically, this load estimator 46 includes a relation setting unit (not shown), in which the relation between the load and the output signal of the supply power meter 45 is set in terms of an arithmetic equation or table, and makes use of the relation setting unit to estimate the load in reference to the output signal so inputted. This load estimator 46 may be provided either in the controller 5 or in an external control device.

Also, the attitude altering drive mechanism 4c is provided with a position detector 47 for detecting an advanced or retracted position of the attitude altering member 31. From the advanced or retracted position of the attitude altering member 31 detected by the position detector 47, a tilted attitude of the distal end member 2 about the X-axis (best shown in FIG. 3B) is determined. In the instance as shown in FIG. 4A, the position detector 47 is made up of a displacement amount measuring unit 48 for measuring the amount of displacement of the pivot lever 43b of the force increasing and transmitting mechanism 43 and a displacement amount estimator 49 for estimating the advanced or retracted position of the attitude altering member 31 from a measured value of the displacement amount measuring unit 48. The pivot lever 43b is a force transmitting member between the attitude altering drive source 42 and the attitude altering member 31. Since the displacement amount measuring unit 48 itself forms the position detector 47, the instance as shown is such that the position detector 47 may be said to be provided between the attitude altering drive source 42 and the attitude altering member 31.

More specifically, the displacement amount measuring unit 48 is a displacement sensor made up of a to-be-detected portion 48a, comprised of a portion of a side face of the pivot lever 43b, and a detecting portion 48b fixed in position to the drive unit housing 4a and operable to detect the displacement of the to-be-detected portion 48a. The detecting portion 48b is, for example, of an optical type, operable to project a detecting beam towards the to-be-detected portion 48a and then to receive reflected rays of light thereof. The side face portion of the pivot lever 43b, which is the to-be-detected portion 48a, is a flat face opposed to the detecting portion 48b. In the instance as shown, although the to-be-detected portion 48a is provided on a side face of the pivot lever 43b remote from the attitude altering member 31, the to-be-detected portion 48a may be provided on a side face adjacent the attitude altering member 31.

The displacement amount estimator 49 has a relation setting unit (not shown), in which a relation between the advanced and retracted positions of the attitude altering member 31 and the output signal of the detecting portion 48b of the displacement amount measuring unit 48 is set by way of calculating equations or tables, and detects the advanced or retracted position of the attitude altering member 31 from an inputted output signal with the use of the relation setting unit referred to above. It is to be noted that this displacement amount estimator 49 may be provided either in the controller 5 or in an external control device.

The controller 5 (best shown in FIGS. 1 and 2) is provided with a tool rotation operating instrument (not shown) for outputting a rotation command signal of the tool 1 and an attitude alteration operating instrument (not shown) for outputting an attitude alteration command signal of the distal end member 2. This controller 5 has an electronic calculating circuit (not shown) and a control program (not shown) built therein and is operable to control the tool rotation drive source 41 and the attitude altering drive source 42 on the basis of the respective command signals from the tool rotation operating instrument and the attitude alteration operating instrument and respective output signals from the load estimator 46 and the displacement amount estimator 49.

The operation of the remote controlled actuator of the structure described hereinabove will now be described with particular reference to FIG. 1 to FIGS. 4A and 4B. When the tool rotating drive source 41 as shown in FIG. 4A is driven, as shown in FIG. 3A, the rotational force thereof is transmitted to the spindle 13 through the rotary shaft 22 to thereby rotate the tool 1 together with the spindle 13. The load acting on the distal end member 2 when the tool 1 then being rotated cuts a bone or the like is estimated from the detection value of the supply power meter 45, shown in FIG. 4A, by the load estimator 46. Accordingly, when the amount of feed of the remote controlled actuator in its entirety and the alteration of attitude of the distal end member 2, as will be described later, are controlled in dependence on the value of the load estimated in the manner described above, cutting of the bone can be properly carried out while the load acting on the distal end member 2 is maintained properly.

During the use, the attitude altering drive source 42 shown in FIG. 4A is driven and the attitude alteration of the distal end member 2 is performed by remote control. By way of example, if the attitude altering member 31 is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 3A. If the attitude altering member 31 is conversely retracted by the attitude altering drive source 42, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 3A. At this time, a pressure from the attitude altering member 31, the elastic repulsive force from the restoring elastic member 32 and a reactive force from the constraint member 21 are applied to the distal end member coupling unit 15 and, depending on the balance of those applied forces, the attitude of the distal end member 2 is determined.

The attitude of the distal end member 2 can be determined from the advanced or retracted position of the attitude altering member 31 detected by the position detector 47 best shown in FIG. 4A. More specifically, by the displacement amount measuring unit 48 which is the displacement sensor, the displacement of the to-be-detected portion 48a, provided in the pivot lever 43b of the force increasing and transmitting mechanism 43, is measured. Then, from the measured value, the displacement amount estimator 49 estimates the angle of rotation of the pivot lever 43b. Once the angle of rotation of the pivot lever 43b is determined, the advanced or retracted position of the attitude altering member 31 is also determined. From the advanced or retracted position of the attitude altering member 31 so detected in the manner described above, the attitude of the distal end member 2 is determined.

Since the position detector 47 is provided in the pivot lever 43b, which is a force transmitting member between the attitude altering drive source 42 and the attitude altering member 31 so that the advanced or retracted position of the attitude altering member 31 is detected at a position near to the attitude altering member 31, the detecting accuracy is high. For example, where the advanced or retracted position of the attitude altering member 31 is desired to be estimated from the amount of activation of the attitude altering drive source 42, deformation and/or rattling motion of the force increasing and transmitting mechanism 43 between the attitude altering drive source 42 and the attitude altering member 31 appear in the form of an error. However, if the detection is made at a position near to the attitude altering member 31, the detecting accuracy increases with the above described error minimized. Since in this way the attitude of the distal end member 2 can be accurately determined, the tip position of the tool 1 can be accurately positioned and as a result, the processing with the tool 1 can be performed accurately.

As shown in FIG. 3A, since the attitude altering member 31 is inserted through the guide hole 30a of the guide pipe 30, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is made up of the wire 31a and the pillar shaped pin 31b and has a flexible property in its entirety, the attitude altering operation of the distal end member 2 is carried out accurately even when the spindle guide section 3 is curved. In addition, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

The remote controlled actuator of the foregoing construction is utilized in grinding the femoral marrow cavity during, for example, the artificial joint replacement surgery and during the surgery, it is used with the distal end member 2 in its entirety or a part thereof inserted into the body of a patient. Because of this, with such distal end member 2 as described above that can be altered in attitude by remote control, the bone can be processed in a condition with the tool 1 maintained in a proper attitude at all times and the opening for insertion of the artificial joint can be finished accurately and precisely.

There is the necessity that the rotary shaft 22 and the attitude altering member 31 are provided within the spindle guide section 3 of an elongated shape in a protected fashion. Hence, as shown in FIG. 3B, the rotary shaft 22 is provided in the center portion of the outer shell pipe 25 and the guide pipe 30, in which the attitude altering member 31 is accommodated, and the reinforcement shafts 34 are arranged between the outer shell pipe 25 and the rotary shaft 22 so as to be juxtaposed in the circumferential direction. Accordingly, it is possible to protect the rotary shaft 22 and the attitude altering member 31 and, at the same time, the interior can be made hollow to thereby reduce the weight without sacrificing the rigidity. Also, the balance as a whole is good.

As shown in FIG. 3A, since the outer diametric surfaces of the rolling bearings 26 supporting the rotary shaft 22 are supported by the guide pipes 30 and the reinforcement shafts 34, the outer diametric surfaces of the rolling bearings 26 can be supported with no need to use any extra member. Also, since the preload is applied to the rolling bearings 26 by means of the spring elements 27A and 27B, the rotary shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

In the embodiment described hereinbefore, the tool rotation drive source 41 and the attitude altering drive source 42 are provided within the common drive unit housing 4a. For this reason, the structure of the remote controlled actuator as a whole can be simplified. It is, however, to be noted that only one of the tool rotation drive source 41 and the attitude altering drive source 42 may be provided within the drive unit housing 4a. Also, as will be explained later, both of the tool rotation drive source 41 and the attitude altering drive source 42 may be provided outside the drive unit housing 4a.

Figure 5:
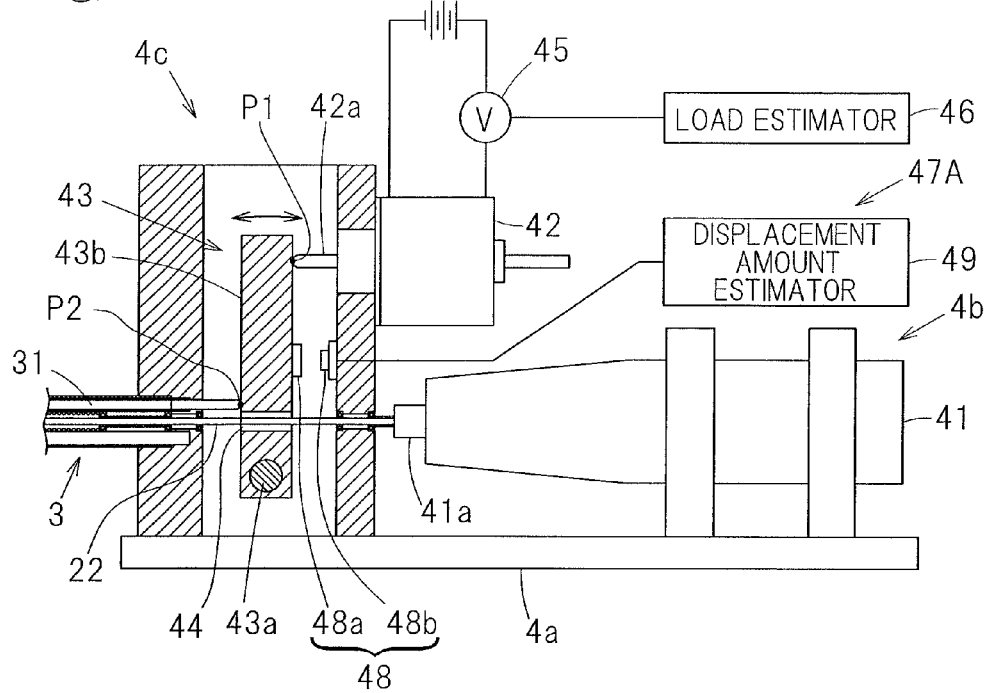
FIG. 5 pertains to a third preferred embodiment of the present invention and is a diagram illustrating a partially sectional view of the tool rotation drive mechanism of a different structure and the attitude altering drive mechanism of a different structure, shown together with the control system.

FIG. 5 illustrates a third preferred embodiment of the present invention, in which the position detector, now identified by 47A, for detecting the advanced or retracted position of the attitude altering member 31 makes use of a different structure. This position detector 47A is such that the displacement amount measuring unit 48 is employed in the form of a displacement sensor of a magnetic type and is made up of a to-be-detected portion 48a, employed in the form of a magnet and provided in the pivot lever 43b of the force increasing and transmitting mechanism 43, and a detecting portion 48b employed in the form of a Hall IC and provided in the drive unit housing 4a in a fashion fixed in position. From a change in magnetic flux detected by the detecting portion 48b, the displacement of the to-be-detected portion 48a is ascertainable. Although, in this embodiment, the to-be-detected portion 48a is provided in a side face of the pivot lever 43b remote from the attitude altering member 31, the to-be-detected portion 48a may be provided in a side face adjacent the attitude altering member 31.

Figure 6:
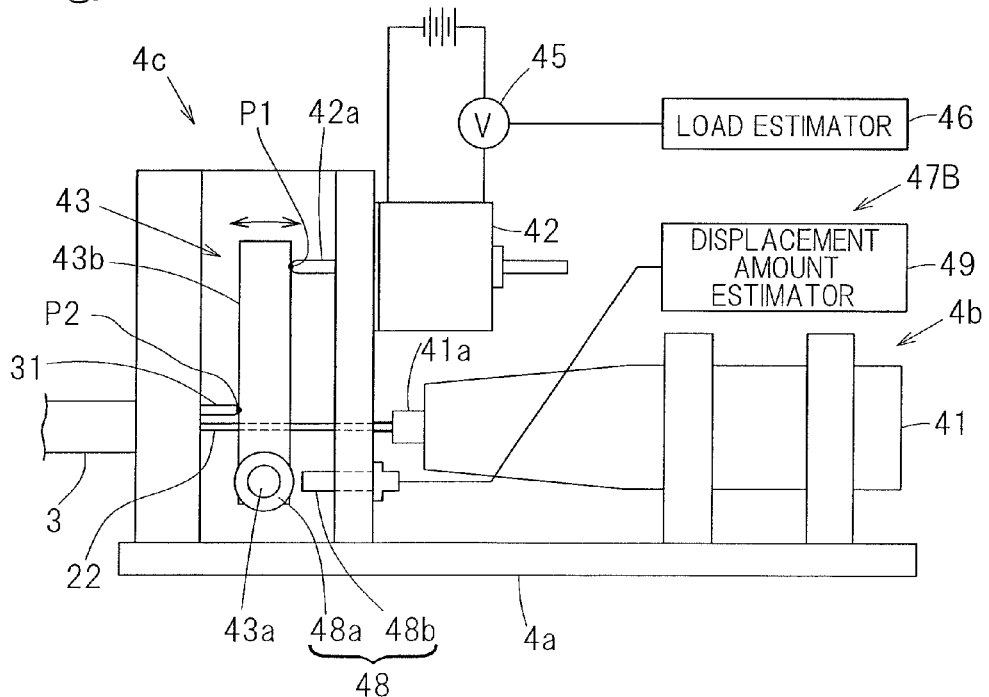
FIG. 6 pertains to a fourth preferred embodiment of the present invention and is a diagram illustrating a partially sectional view of the tool rotation drive mechanism of another different structure and the attitude altering drive mechanism of another different structure, shown together with the control system.

FIG. 6 illustrates a fourth preferred embodiment of the present invention, in which the position detector, now identified by 47B, has a further different structure. This position detector 47B is such that the displacement amount measuring unit 48 is employed in the form of an angle sensor for detecting the angle of rotation of the pivot lever 43b of the force increasing and transmitting mechanism 43. More specifically, the displacement amount measuring unit 48 is made up of a to-be-detected portion 48a, employed in the form of a rotary encoder rotatable together with the pivot lever 43b and having a plurality of scale grids provided equidistantly on the circumference coaxial with the pivot pin 43a, and a detecting portion 48b fixed in position to the drive unit housing 4a and operable to read the scale grids referred to above. This angle sensor may be of either an optical type or a magnetic type. The displacement amount estimator 49 estimates the angle of pivot of the pivot lever 43b from a read value of the detecting portion 48b and also estimates the advanced or retracted position of the attitude altering member 31 from the angle of pivot of the pivot lever 43b. From the advanced or retracted position of the attitude altering member 31 so estimated in the manner described above, the attitude of the distal end member 2 is determined. Although in this embodiment, the detecting portion 48b is provided in a side face of the drive unit housing 4a remote from the attitude altering member 31, the detecting portion 48b may be provided in a side face adjacent the attitude altering member 31.

Figure 7:
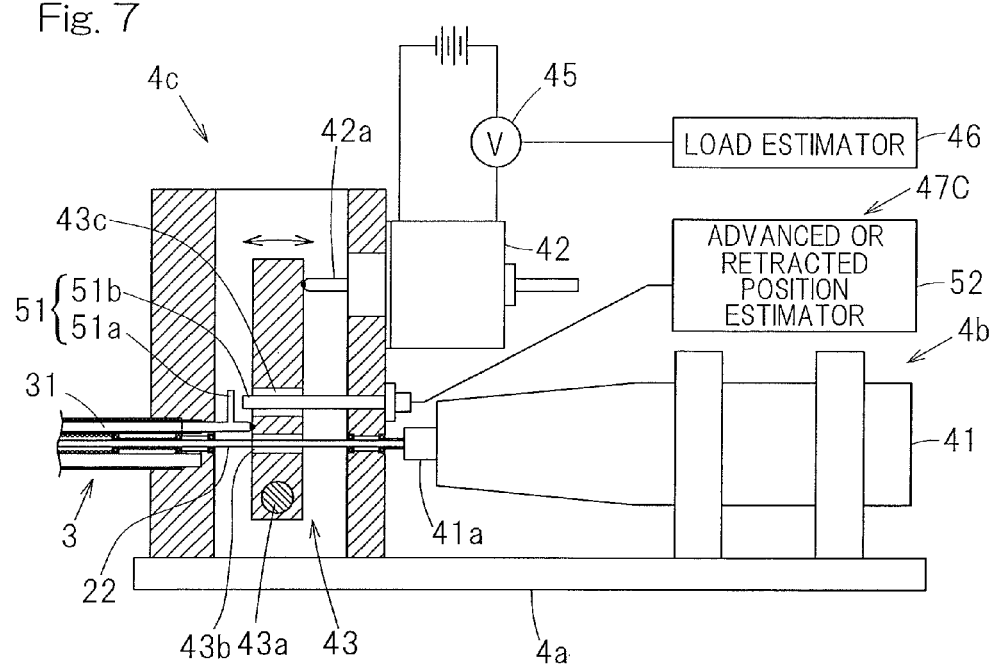
FIG. 7 pertains to a fifth preferred embodiment of the present invention and is a diagram illustrating a partially sectional view of the tool rotation drive mechanism of a further different structure and the attitude altering drive mechanism of a further different structure, shown together with the control system.

FIG. 7 illustrates a fifth preferred embodiment of the present invention, in which the position detector, now identified by 47C, has a still different structure. Unlike that employed in the practice of any one of the respective embodiments shown in and described with reference to FIGS. 4A and 4B to FIG. 6, the position detector 47C is made up of an advanced or retracted position measuring unit 51 for measuring the advanced or retracted position of one end of the attitude altering member 31 adjacent the drive unit housing 4a, and an advanced or retracted position estimator 52 for estimating the advanced or retracted position of the attitude altering member 31 from a measured value of the advanced or retracted position measuring unit 51. The advanced or retracted position measuring unit 51 itself functions as a position detector 47 and, therefore, in this embodiment, the position detector 47 may be said to be provided in the attitude altering member 31.

More specifically, the advanced or retracted position measuring unit 51 is made up of a to-be-detected 51a, provided at one end of the attitude altering member 31 adjacent the drive unit housing 4a and having a flat face perpendicular to the lengthwise direction of the attitude altering member 31, and a detecting portion 51b fixed in position to the drive unit housing 4a and operable to detect the displacement of the to-be-detected portion 51a. The detecting portion 51b is, for example, of an optical type, operable to project a detection light beam towards the to-be-detected portion 51a and then to receive reflected light thereof In the instance as shown, the detecting portion 51b is fitted to a side face of the drive unit housing 4a remote from the spindle guide section 3 and extends towards a spindle guide section 3 side, after having passed through a throughhole 43c defined in the pivot lever 43b of the force increasing and transmitting mechanism 43, with a tip thereof confronting the to-be-detected portion 51a. Although, in this embodiment, the to-be-detected portion 51a has been shown and described as formed integrally with the pin 31b of the attitude altering member 31, the to-be-detected portion 51a may be a member separate from the pin 31b and may be fixed to the wire 31a or the pin 31b of the attitude altering member 31 by means of welding or press-fitting.

The advanced or retracted position estimator 52 has a relation setting unit (not shown), in which a relation between the advanced and retracted position of the attitude altering member 31 and an output signal of the detecting portion 51b of the advanced or retracted position measuring unit 51 are set by way of calculating equations or tables, and detects the advanced or retracted position of the attitude altering member 31 from an inputted output signal with the use of the relation setting unit referred to above. It is to be noted that this advanced or retracted position estimator 52 may be provided either in the controller 5 or in an external control device.

From a measured value of the advanced or retracted position measuring unit 51, the advanced or retracted position estimator 52 estimates the advanced or retracted position of the attitude altering member 31. From the advanced or retracted position of the attitude altering member 31 so estimated in the manner described above, the attitude of the distal end member 2 is determined. If in this way the advanced or retracted position of the attitude altering member 31 is measured directly, deformation and/or rattling motion of the force increasing and transmitting mechanism 43 do not appear in the form of an error and as a result, the detecting accuracy is therefore high. For this reason, the attitude of the distal end member 2 can be further accurately determined.

Figure 8:
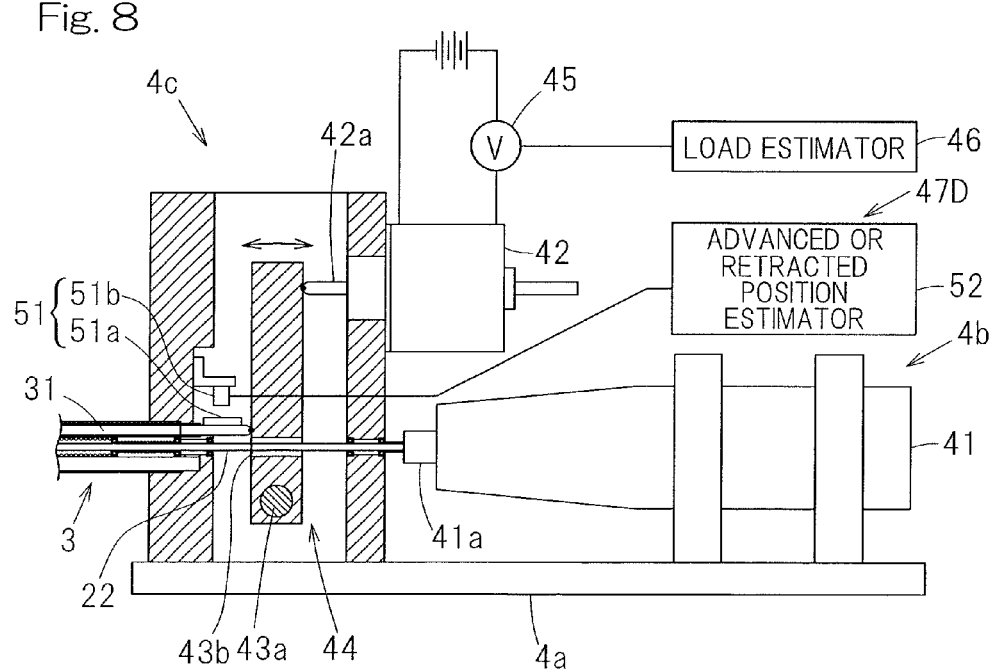
FIG. 8 pertains to a sixth preferred embodiment of the present invention and is a diagram illustrating a partially sectional view of the tool rotation drive mechanism of a still further different structure and the attitude altering drive mechanism of a still further different structure, shown together with the control system.

FIG. 8 illustrates a sixth preferred embodiment of the present invention, in which the position detector, now identified by 47D, for directly measuring the advanced or retracted position of the attitude altering member 31 has a different structure. This position detector 47D is made up of a to-be-detected portion 51a, employed in the form of a linear encoder provided at an end portion of the attitude altering member 31 adjacent to the drive unit housing 4a and having scale grids to be detected arranged in a direction conforming to the lengthwise direction of the attitude altering member 31, and a detecting portion 51b fixed in position to the drive unit housing 4a and operable to read the scale grids of the to-be-detected portion 51a. Even in this case, in a manner similar to that described previously, the detecting accuracy of the advanced or retracted position of the attitude altering member 31 is high and the attitude of the distal end member 2 can be determined accurately.

FIGS. 9 to 12 illustrate a seventh preferred embodiment of the present invention, which make use of the tool rotation drive mechanism of a different structure and the attitude altering drive mechanism of a different structure. While in any one of the previously described embodiments, the tool rotation drive source 41 of the tool rotation drive mechanism 4b and the attitude altering drive source 42 of the attitude altering drive mechanism 4c are provided within the drive unit housing 4a, the embodiment shown in FIGS. 9 to 12 is such that the tool rotation drive source 41 and the attitude altering drive source 42 are provided within a drive source housing 60, which is a member separate from the drive unit housing 4a.

Figure 11:
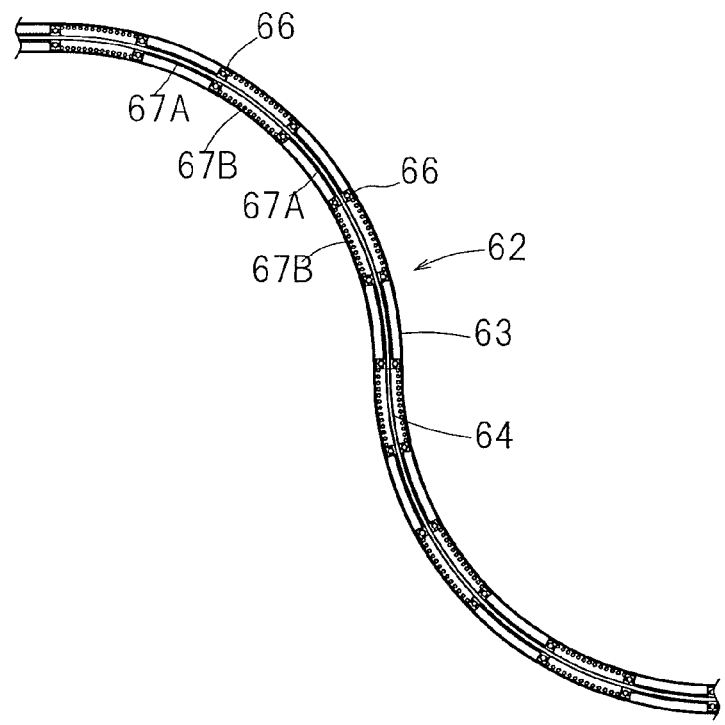
FIG. 11 is a sectional view showing a tool rotating cable employed in the tool rotation drive mechanism.

The tool rotation drive mechanism, now identified by 61, that is employed in the practice of this seventh embodiment is operable to transmit the rotation of the output shaft 41a of the tool rotation drive source 41, provided in the drive source housing 60, to a base end of the rotary shaft 22 within the drive unit housing 4a by means of an inner wire 64 (shown in FIG. 11) of a tool rotating cable 62. For example, the tool rotating cable 62 may have such a structure as shown in FIG. 11. In other words, at a center of a flexible outer tube 63, the flexible inner wire 64 referred to above is rotatably supported by a plurality of rolling bearings 66. The inner wire 64 has its opposite ends connected respectively with base ends of the output shaft 41a of the tool rotation drive source 41 and the rotary shaft 22. Between the neighboring rolling bearings 66, spring elements 67A and 67B are provided for generating preloads to the rolling bearings 66. Those spring elements 67A and 67B are employed in the form of, for example, compression coil springs. Those spring elements include an inner ring spring element 67A for applying the preload to an inner ring of each of the rolling bearings 66 and an outer ring spring element 67B for applying the preload to an outer ring of each of the rolling bearings 66, and those spring elements 67A and 67B are disposed alternately relative to each other. With the preloads having been applied from the spring elements 67A and 67B to the rolling bearings 66 in this way, the inner wire 64 can be rotated at a high speed. A commercially available flexible shaft may be employed for the tool rotating cable 62.

Also, the attitude altering drive mechanism 71 employed in the practice of the seventh embodiment is such that the attitude altering drive source 42 provided in the drive source housing 60 is employed in the form of a rotary actuator, and the rotation of this attitude altering drive source 42 is transmitted to a rotation/advance or retraction converting and transmitting mechanism 80 within the drive unit housing 4a by means of an inner wire 74 (best shown in FIG. 12) of an attitude altering cable 72. The details of the rotation/advance or retraction converting and transmitting mechanism 80 will be described later.

Figure 12:
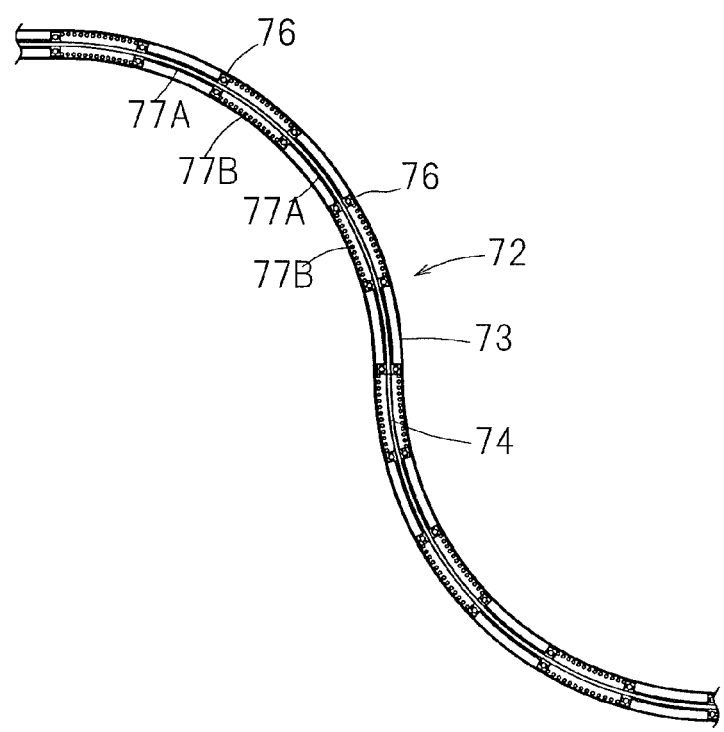
FIG. 12 is a sectional view showing an attitude altering cable employed in the attitude altering drive mechanism.

The attitude altering cable 72 is of the same structure as the tool rotating cable 62 and takes such a structure as shown in FIG. 12. In other words, at a center of a flexible outer tube 73, the flexible inner wire 74 is rotatably supported by a plurality of rolling bearings 76. The inner wire 74 has its opposite ends connected respectively with the output shaft 42a of the attitude altering drive source 42 and a selective advancing and retracting member 81. Between the neighboring rolling bearings 76, spring elements 77A and 77B are provided for generating preloads to the rolling bearings 76. Those spring elements 77A and 77B are employed in the form of, for example, compression coil springs. There are an inner ring spring element 77A for applying the preload to an inner ring of each of the rolling bearings 76 and an outer ring spring element 77B for applying the preload to an outer ring of each of the rolling bearings 76, and those spring elements 77A and 77B are disposed alternately relative to each other. With the preloads having been applied from the spring elements 77A and 77B to the rolling bearings 76 in this way, the inner wire 74 can be rotated at a high speed. A commercially available flexible shaft may be employed for the attitude altering cable 72.

Figure 10:
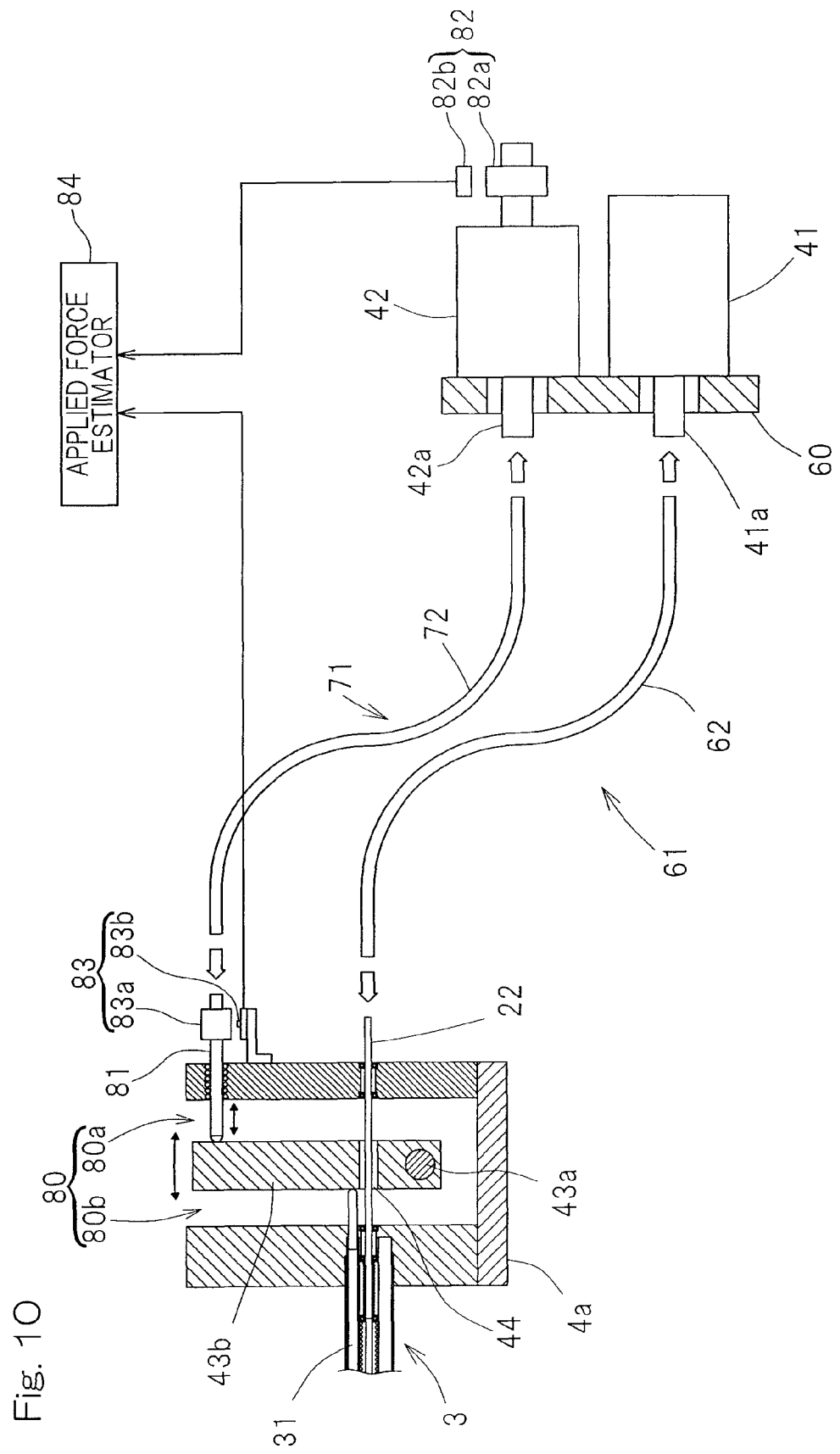
FIG. 10 is a diagram illustrating a partially sectional view of the tool rotation drive mechanism and the attitude altering drive mechanism, shown together with the control system.

As shown in FIG. 10, the rotation/advance or retraction converting and transmitting mechanism 80 is made up of a rotation/advance or retraction converting unit 80a and a force increasing and transmitting unit 80b. The rotation/advance or retraction converting unit 80a is operable to convert the rotation of the attitude altering drive source 42, transmitted through the inner wire 74, into an advancing or retracting operation in a linear direction and is comprised of, for example, a screw mechanism such as, for example, a ball screw. More specifically, the rotation of the advancing and retracting member 81 rotatable together with the inner wire 74 is converted into the advancing or retracting operation relative to the drive unit housing 4a by the effect of the screw mechanism. The force increasing and transmitting unit 80b corresponds to the force increasing and transmitting mechanism 43, employed in the practice of the previously described embodiments, and a spherical tip of the advancing and retracting member 81 is held in contact with a side face of the pivot lever 43b thereof. Various parts of the force increasing and transmitting unit 80b are designated by reference numerals used to indicate like parts of the force increasing and transmitting mechanism 43.

This attitude altering drive mechanism 71 is provided with an activation amount measuring unit 82 for measuring the amount of activation of the attitude altering drive source 42. In the case of the embodiment now under discussion, the activation amount measuring unit 82 is a rotation sensor for measuring the amount of rotation of the attitude altering drive source 42, which is a rotary actuator, and is made up of a rotary encoder as a to-be-detected portion 82a, provided on an outer periphery of the output shaft 42a of the attitude altering drive source 42, and a detecting portion 82b fixed in position to the drive source housing 60 and operable to read scale grids of the rotary encoder.

Also, the attitude altering drive mechanism 71 is provided with a displacement amount measuring unit 83 for measuring the amount of displacement of a force transmitting member between the attitude altering drive source 42 and the attitude altering member 31. The displacement amount measuring unit 83 is a position detector for detecting the advanced or retracted position of the attitude altering member 31 from the amount of displacement of the force transmitting member. In the instance as shown, the displacement amount measuring unit 83 is a rotation sensor for detecting the amount of rotation of the advancing and retracting member 81, which is a force transmitting member, and is made up of a rotary encoder as a to-be-detected portion 83a, provided on an outer periphery of the advancing and retracting member 81, and a detecting portion 83b fixed in position to the drive unit housing 4a and operable to read scale grids of the rotary encoder.

Respective measured values of the activation amount measuring unit 82 and the displacement amount measuring unit 83, both referred to above, are transmitted to an applied force estimator 84. The applied force estimator 84 estimates the magnitude of a force, which the attitude altering member 31 applies to the distal end member 2, from the difference between the advanced or retracted position of the attitude altering member 31, estimated from the amount of activation of the attitude altering drive source 42 that is measured by the activation amount measuring unit 82, and the advanced or retracted position of the attitude altering member 31 estimated from the measured value of the displacement amount measuring unit 83.

More specifically, the applied force estimator 84 has a relation setting unit (not shown), in which the relation between both of the measured value of the attitude altering drive source 42 and the measured value of the displacement amount measuring unit 83 and the magnitude of the force applied to the distal end member 2 by the attitude altering member 31 is set by way of calculating equations or tables, and is operable to detect the magnitude of the force, which the attitude altering member 31 applies to the distal end member 2, from the inputted measured value with the use of the relation setting unit. By controlling an output of the attitude altering drive source 42 in dependence on the magnitude of the applied force so estimated, alteration of the attitude of the distal end member 2 can be safely and accurately accomplished. It is, however, to be noted that the applied force estimator 84 may be provided in the controller 5 or, alternatively, in an external control device.

Deformation and rattling motion of the force transmitting member between the attitude altering drive source 42 and the attitude altering member 31 change with a change of the magnitude of the force the force transmitting member applies to the attitude altering member 31. More specifically, if the force applied to the attitude altering member 31 increases, the deformation of the force transmitting member also increases. In other words, the larger the force applied to the attitude altering member 31, the larger the difference between the advanced or retracted position of the attitude altering member 31, which is estimated from the amount of activation of the attitude altering drive source 42, and the advanced or retracted position of the attitude altering member 31, which is estimated by the displacement amount measuring unit 83. The magnitude of the force applied to the attitude altering member 31 by the force transmitting member is nothing other than the magnitude of the force the attitude altering member 31 applies to the distal end member 2. Accordingly, from the magnitude of the difference of the above discussed retracted or advanced positions, the magnitude of the force applied to the distal end member 2 by the attitude altering member 31 can be estimated.

In particular, in the case of this embodiment in which as the force transmitting member the flexible attitude altering cable 72 is employed, as a result of twisting of the inner wire 74 of the attitude altering cable 72, a phase difference occurs between input and output sides of the inner wire 74. Since the phase difference brought about by the twisting of the inner wire 74 occurs more markedly than the displacement caused upon deformation of any other force transmitting member, for example, the pivot lever 43b, the magnitude of the force the attitude altering member 31 applies to the distal end member 2 can be easily estimated with use of the above described phase difference.

It is to be noted that for the displacement amount measuring unit, either the advanced or retracted position measuring unit 51 or the displacement amount measuring unit 48 of the position detectors 47 to 47D shown in FIGS. 4A and 4B to FIG. 8, although the both are not shown, may be employed in place of that employed in the practice of the seventh embodiment shown in FIG. 10. Also, separate from the displacement amount measuring unit 83 shown in FIG. 10, the use may be made of either the advanced or retracted position measuring unit 51 or the displacement amount measuring unit 48 of the position detectors 47 to 47D shown in FIGS. 4A and 4B to FIG. 8, so that the advanced or retracted position of the attitude altering member 31 estimated from the measured value of the activation amount measuring unit 82 can be corrected with the utilization of the measured value of the displacement amount measuring unit 48, although this is not shown. If such a correction is performed, the accuracy of the advanced or retracted position of the attitude altering member 31 estimated from the measured value of the activation amount measuring unit 82 can be enhanced.

Figure 9:
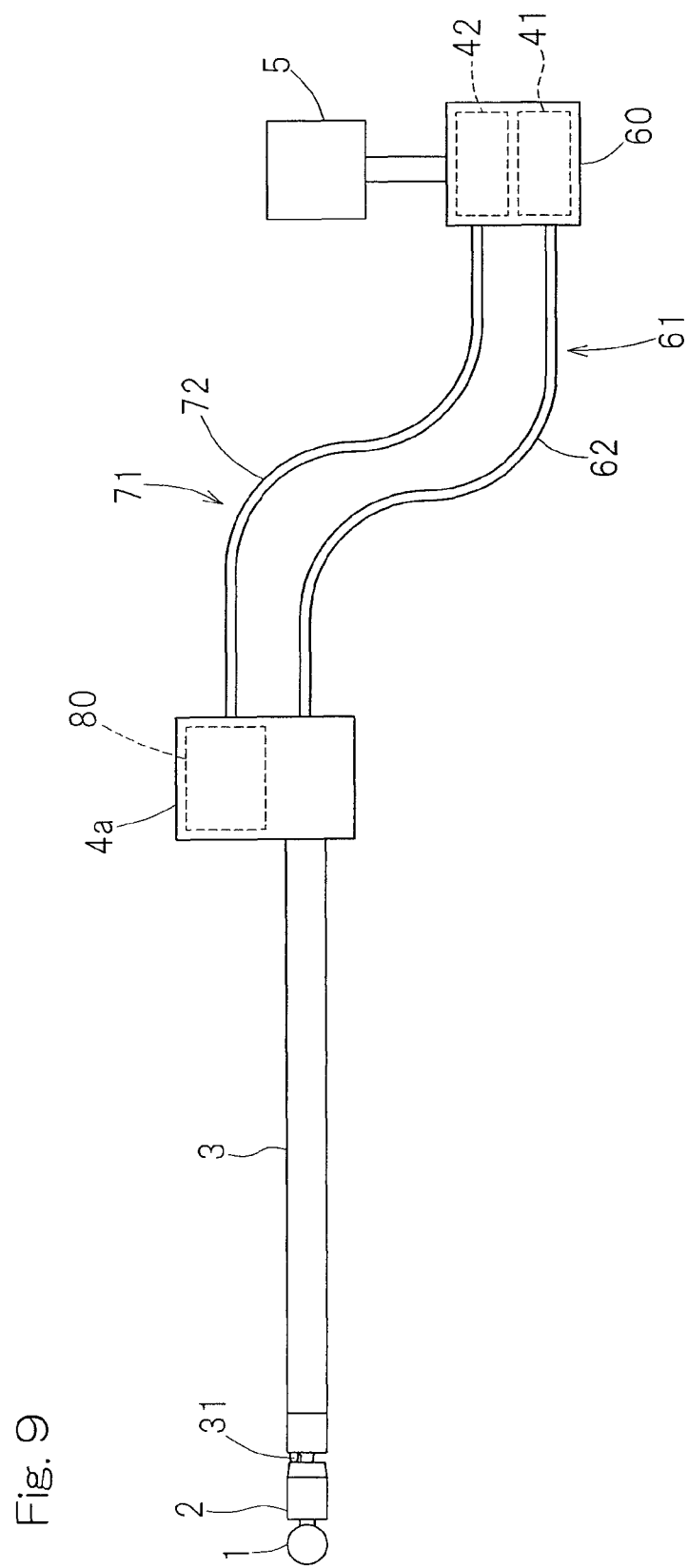
FIG. 9 is a diagram showing a schematic structure of the remote controlled actuator designed in accordance with a seventh preferred embodiment of the present invention.

As shown in FIG. 9, the controller 5 for controlling the tool rotation drive source 41 and the attitude altering drive source 42 is connected with the drive source housing 60. Each of the distal end member 2 and the spindle guide section 3 are of the same structure as that employed in the practice of any one of the previously described embodiments.

When, as is the case with this seventh embodiment, the tool rotation drive source 41 and the attitude altering drive source 42 are provided outside the drive unit housing 4a, the drive unit housing 4a can be made compact. For this reason, the handleability at the time the remote controlled actuator is operated with the drive unit housing 4a carried by an operator can be increased. Since each of the tool rotation drive source 41 and the attitude altering drive source 42 is employed in the form of the rotary actuator, respective rotations of the tool rotation drive source 41 and the attitude altering drive source 42, both outside the drive unit housing 4a, can be easily transmitted to the rotary shaft 22 within the drive unit housing 4a and the rotation/advance or retraction converting and transmitting mechanism 80.

Figure 13A:
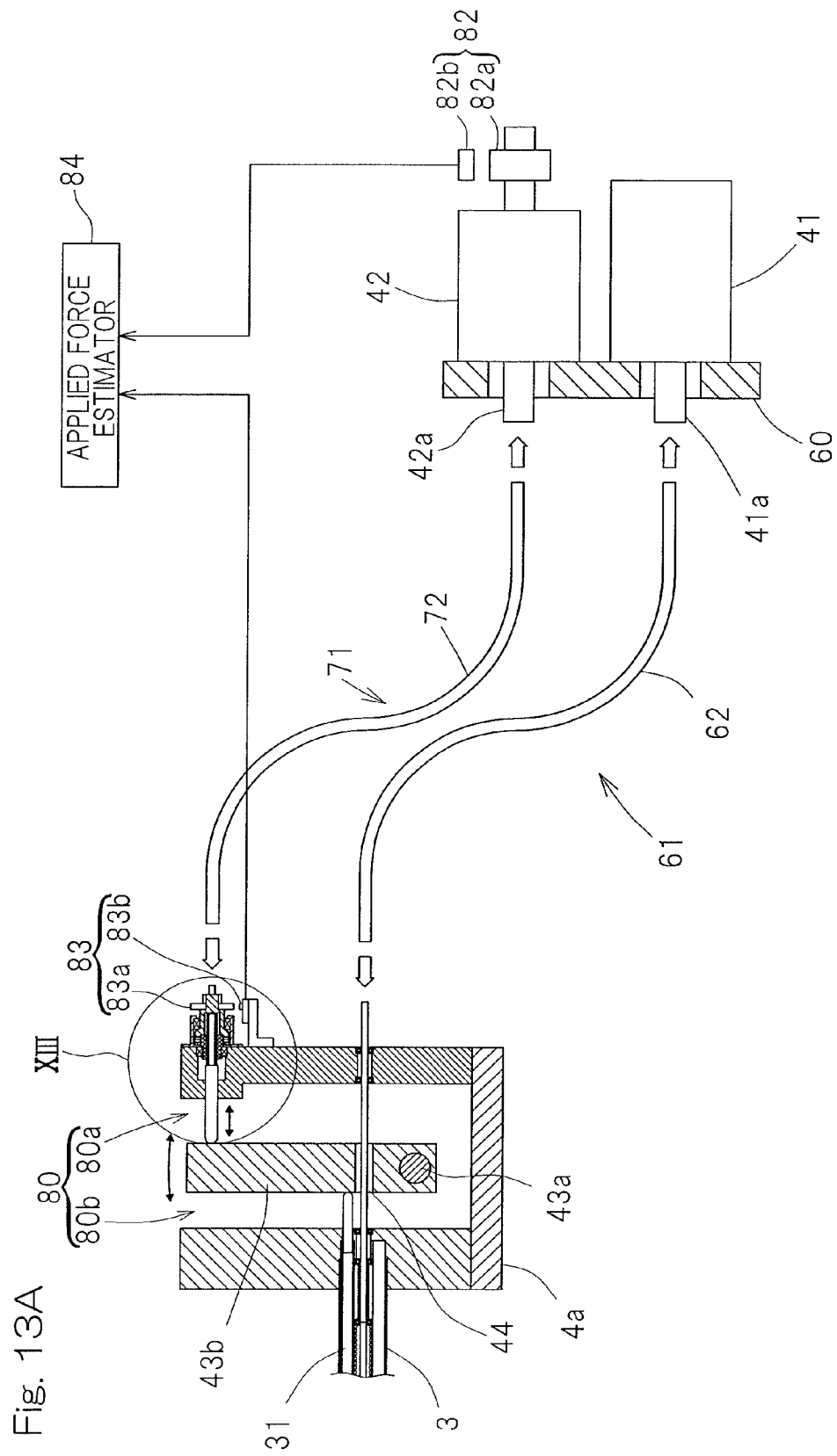
FIG. 13A pertains to an eighth preferred embodiment of the present invention, in which the remote controlled actuator makes use of the attitude altering drive mechanism of a different structure, and is a diagram illustrating a partially sectional view of the tool rotation drive mechanism and the attitude altering drive mechanism shown together with the control system.
Figure 13B:
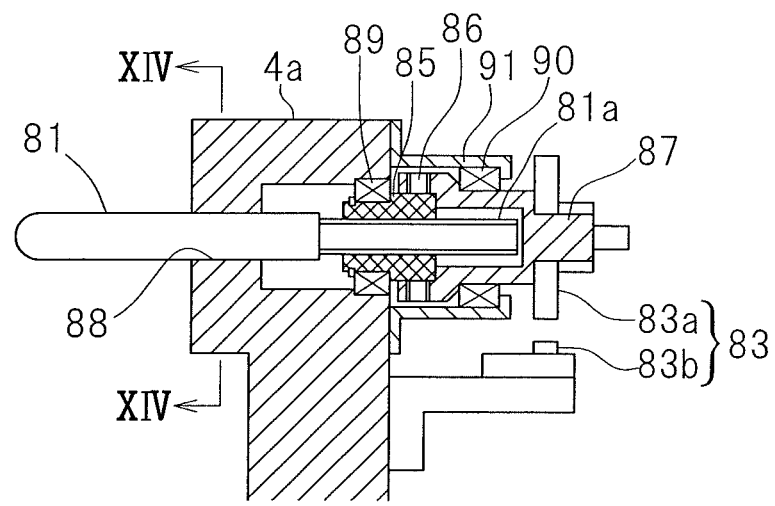
FIG. 13B is an enlarged diagram showing a portion of FIG. 13A that is encompassed by the circle XIII.
Figure 14:
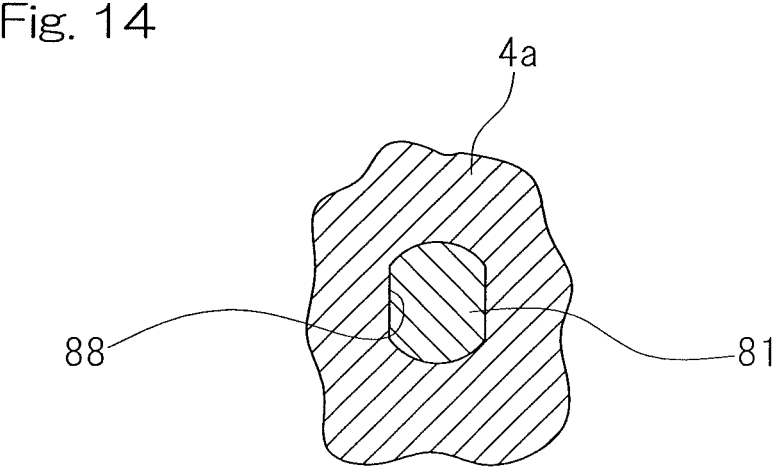
FIG. 14 is a cross sectional view taken along the line XIV-XIV in FIG. 13B.

The rotation/advance or retraction converting unit 80a of the rotation/advance or retraction converting and transmitting mechanism 80 may be of a structure as shown in FIGS. 13A and 13B illustrating an eighth preferred embodiment of the present invention. In other words, this rotation/advance or retraction converting unit 80a is, as shown in FIG. 13B, includes a selective advancing and retracting member 81 provided reciprocally movably in the drive unit housing 4a, a female screw member 85 engaged with a male screw portion 81a of this advancing and retracting member 81, and a connecting member 87 coupled with an outer periphery of the female screw member 85 by means of a connecting pin 86. As shown in FIG. 14, the advancing and retracting member 81 has a sectional shape, in which opposite side faces thereof are cut out to render them to be flat faces, and, when inserted into a throughhole 88 in the drive unit housing 4a, which is of a sectional shape complemental to the sectional shape of the advancing and retracting member 81, it can be selectively advanced or retracted in a direction conforming to the direction of a center axis, but non-rotatable about the center axis. Referring to FIG. 13B, the female screw member 85 is rotatably supported by the drive unit housing 4a through a bearing 89 and the connecting member 87 is rotatably supported by a support member 91 fixed to the drive housing 4a through a bearing 90. The connecting member 87 is connected with the inner wire 74 of the attitude altering cable 72. For example, as shown in, FIG. 13B, it is recommended that the displacement amount measuring unit 83 for measuring the amount of displacement between the attitude altering drive source 42 and the attitude altering member 31 is so structured that the use may be made of a rotary encoder, as the to-be-detected portion 83a, on an outer periphery of the connecting member 87 and the scale grids of the rotary encoder may be read by the detecting portion 83b provided in the drive unit housing 4a in a fashion fixed in position.

According to the above described construction, the connecting member 87 and the female screw member 85 rotate together with the inner wire 74 and, due to engagement between the female screw member 85 and the screw portion 81a of the advancing and retracting member 81, the advancing and retracting member 81 is selectively advanced or retracted. Since the advancing and retracting member 81 is supported non-rotatably about the center axis, the advancing and retracting member 81 does not apply any other force than a pressing force to the pivot lever 43b of the force increasing and transmitting unit 80b and, therefore, the force increasing and transmitting unit 80b will hardly fail to operate.

FIGS. 15A and 15B illustrate a ninth preferred embodiment of the present invention, in which a different structure is employed for altering the attitude of the distal end member 2. This remote controlled actuator includes two guide pipes 30 spaced 180 degrees in phase relative to each other within an outer shell pipe 25 and each of the guide pipes 30 has an inner diametric hole functioning as a guide hole 30a within which an attitude altering member 31 comprised of the wire 31a and the pillar shaped pins 31b in a manner similar to those described hereinbefore is inserted for advancement and retraction. Between those two guide pipes 30, a plurality of reinforcement shafts 34 are arranged on the same pitch circle diameter C as that of the guide pipes 30. No restoring elastic member 32 is provided. The guide faces F1 and F2 are spherical surfaces each having the center of curvature lying at the point O or cylindrical surfaces each having a lateral X-axis as a longitudinal axis passing through the point O.

The drive unit 4 (not shown) is provided with two attitude altering drive sources 42 (not shown) for selectively advancing and retracting respective attitude altering members 31 so that when those two attitude altering drive sources 42 are driven in respective directions opposite to each other, the distal end member 2 can be altered in attitude. By way of example, when the upper attitude altering member 31 shown in FIG. 15A is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards as viewed in FIG. 15A. Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 15A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces. According to this construction, since the housing 11 for the distal end member 2 is pressed by the two attitude altering members 31, as compared with the previously described embodiment in which it is pressed by a single attitude altering member 31, the attitude stability of the distal end member 2 can be increased.

FIGS. 16A and 16B illustrate a tenth preferred embodiment, in which the structure for altering the attitude of the distal end member 2 is further different. In this remote controlled actuator, as best shown in FIG. 16B, three guide pipes 30 are employed and arranged at respective circumferential locations spaced 120° in phase from each other within the outer shell pipe 25, and the attitude altering member 31 is reciprocally movably inserted in each of the guide holes 30a, which are inner diametric holes of such guide holes 30a, in a manner similar to that described hereinbefore. Among the three guide pipes 30, a plurality of reinforcement shafts 34 are arranged on the same pitch circle C as that of the guide pipes 30. No resilient restoring member 32 is employed. As shown in FIG. 16A, the guide faces F1 and F2 represent spherical faces having a center of curvature at a point O and the distal end member 2 can be tilted in any arbitrarily chosen direction.

Figure 18:
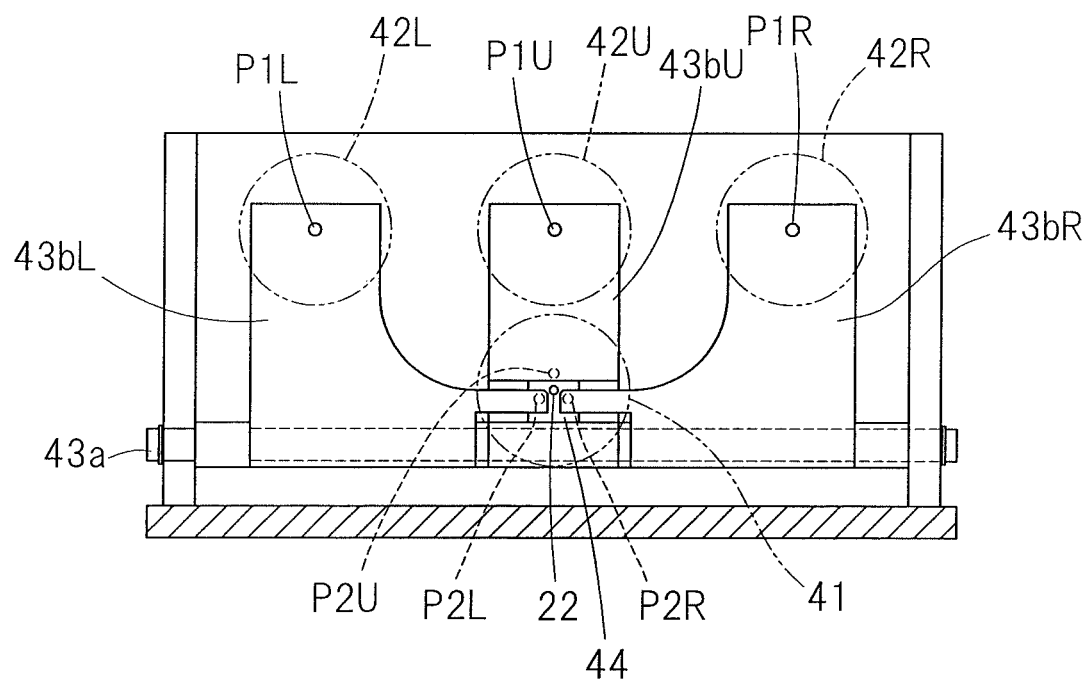
FIG. 18 is a diagram showing a structure of the attitude altering drive mechanism employed in the remote controlled actuator shown in any of FIGS. 16A and 16B and FIGS. 17A and 17B.

The drive unit 4 is provided with three attitude altering drive sources 42 (42U, 42L and 42R), best shown in FIG. 18, for selectively advancing or retracting respective attitude altering members 31 (31U, 31L and 31R) and, accordingly, the attitude of the distal end member 2 is altered by driving those three attitude altering drive sources 42 in liaison with each other. By way of example, when one of the attitude altering members 31U, upper side one as viewed in FIG. 16B, is advanced towards the distal, tip end side while the other two attitude altering members 31L and 31R are retracted, the housing 11 for the distal end member 2 is pressed by the upper attitude altering member 31U to allow the distal end member 2 to be altered in attitude along the guide surfaces F1 and F2 with the distal, tip end side consequently oriented downwardly as viewed in FIG. 16A. At this time, those attitude altering drive sources 42 are controlled so that the amount of advance or retraction of each of the attitude altering members 31 may become proper. On the other hand, when each of those attitude altering members 31 is retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 16A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 16A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased. If the number of the attitude altering members 31 is increased, the attitude stability of the distal end member 2 can be yet further increased.

Figure 17A:
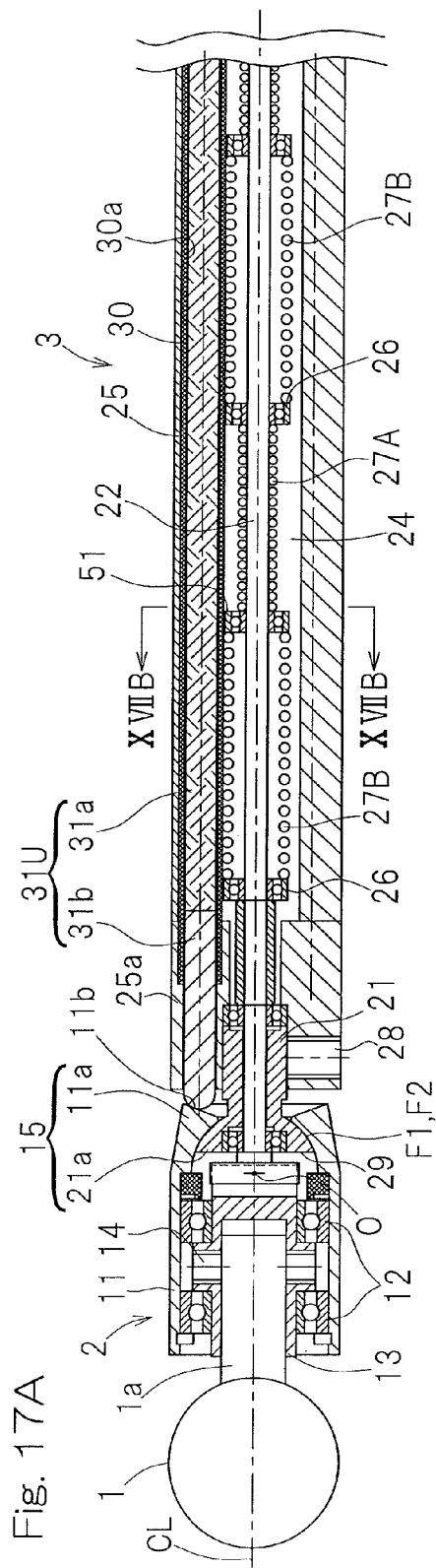
FIG. 17A is a longitudinal sectional view showing the distal end member and the spindle guide section, both employed in the remote controlled actuator designed in accordance with an eleventh preferred embodiment of the present invention, in which a still further different mechanism for altering the attitude of the distal end member is employed.
Figure 17B:
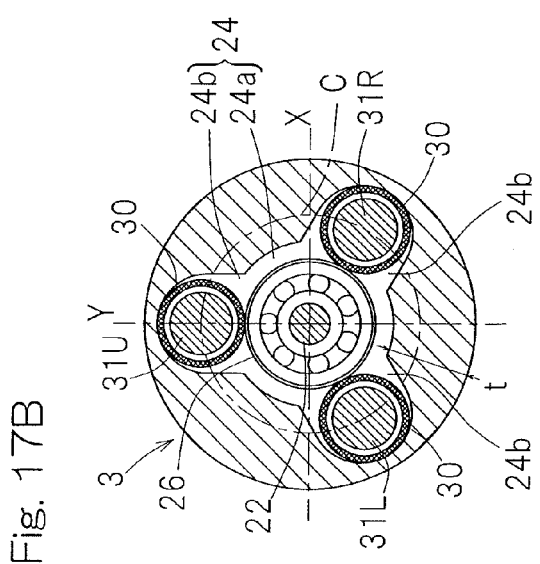
FIG. 17B is a cross sectional view taken along the line XVIIB-XVIIB in FIG. 17A.

FIGS. 17A and 17B illustrate an eleventh preferred embodiment of the present invention, in which the spindle guide section 3 has an internal structure different from that shown in and described with reference to FIGS. 16A and 16B. The spindle guide section 3 employed in this remote controlled actuator is such that the outer shell pipe 25 has a hollow hole 24 made up of a round hole portion 24a at a center thereof and three grooved portions 24b formed on an outer periphery of the round hole portion 24a so as to be depressed radially outwardly from respective circumferential positions spaced 120° from each other. Each of the grooved portions 24b has a tip, a peripheral wall of which represents a semicircular shape in section. The rotary shaft 22 and the rolling bearings 26 are accommodated within the round hole portion 24a, and the attitude altering member 31 (31U, 31L and 31R) is accommodated within each of grooved portions 24b.

Since the outer shell pipe 25 is made to have the above described sectional shape, the wall thickness t of portions of the outer shell pipe 25 other than the grooved portions 24b increases and as a result, the geometrical moment of inertia of the outer shell pipe 25 becomes large. In other words, the rigidity of the spindle guide section 3 is increased. Accordingly, not only can the positioning accuracy of the distal end member 2 be increased, but the cutting capability can also be increased. Also, since the guide pipes 30 are arranged within the grooved portions 24b, the positioning of the guide pipes 30 in the circumferential direction can be facilitated and as a result, the assemblability is good.

Where the attitude altering members 31 are provided at the three circumferential locations such as shown in FIGS. 16A and 16B and FIGS. 17A and 17B, the attitude altering drive mechanism 4c may be so constructed as shown in, for example, FIG. 18. In other words, the three attitude altering drive sources 42 (42U, 42L and 42R) for selectively advancing or retracting the respective attitude altering members 31 (31U, 31L and 31R) are arranged leftwards and rightwards in parallel to each other and, at the same time, the lever 43b (43bU, 43bL and 43bR) corresponding to each of the attitude altering drive sources 42 is pivotally mounted around a common support pin 43a. Further, The force increasing and transmitting mechanism 43 is so designed and so configured as to allow a force of the output rods 42a (42aU, 42aL, 42aR) of the respective attitude altering drive sources 42 to work on a working point P1 (P1U, P1L, P1R) of the levers 43b, which are respectively spaced a long distance from the support pin 43a, and as to apply a force to the attitude altering members 31 at a force point P2 (P2U, P2L, P2R), which are spaced a short distance from the support pin 43a. Accordingly, the outputs of the attitude altering drive sources 42 can be increased and then transmitted to the attitude altering members 31. Since the use of the force increasing and transmitting mechanism 43 is effective to enable a large force to be applied to the attitude altering members 31 even in the linear actuator of a low output capability, the linear actuator can be downsized. It is to be noted that the rotary shaft 22 is extended through an opening 44 defined in the pivot lever 43bU associated drivingly with the upper attitude altering member 31U.

Although the spindle guide section 3 employed in the practice of any one of the foregoing embodiments has been shown and described as having a linear shape, the remote controlled actuator of the present invention is effective in that even when the attitude altering member 31 is flexible and the spindle guide section 3 has a curved portion, the attitude alteration operation of the distal end member 2 is assuredly effected and, therefore, a portion of or the whole of the spindle guide section 3 may be so formed as to have a curved shape as shown in FIG. 2. If the spindle guide section 3 is of a curved configuration, it may occur that the distal end member 2 can be inserted deep into the bone where it fails to reach if having a linear shape, and the processing of the artificial joint insertion hole during the artificial joint replacement surgery can be precisely finished.

Where the spindle guide section 3 is so formed as to have the curved shape, the outer shell pipe 25, the guide pipe 30 and the reinforcement shaft 34 have to be curved in shape correspondingly. Also, the use of an easily deformable material for the rotary shaft 22 is preferred and, for example, a shape memory alloy can be suitably employed therefor.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . Tool
2 . . . Distal end member
3 . . . Spindle guide section
4a . . . Drive unit housing
5 . . . Controller
13 . . . Spindle
15 . . . Distal end member connecting unit
22 . . . Rotary shaft
30a . . . Guide hole
31 . . . Attitude altering member
41 . . . Tool rotation drive source 42 ... Attitude altering drive source
42a ... Output rod
43 ... Force increasing and transmitting mechanism
43b ... Pivot lever (Force transmitting member)
47 ... Position detector
48 ... Displacement amount measuring unit
48a ... To-be-detected portion
48b ... Detecting portion
49 ... Displacement amount estimator
51 ... Advanced or retracted position measuring unit
51a ... To-be-detected portion
51b ... Detecting portion
52 ... Advanced or retracted position estimator
72 ... Attitude altering cable (Force transmitting member)
80 ... Rotation/advance or retraction converting and transmitting mechanism
81 ... Selective advancing and retracting member (Force transmitting member)
82 ... Activation amount measuring unit
83 ... Displacement amount measuring unit (Position detector)
84 ... Applied force estimator

What is claimed is:

1. A remote controlled actuator which comprises:
a spindle guide section of an elongated shape;
a distal end member fitted to a tip of the spindle guide section through a distal end member connecting unit for alteration in attitude;
a tool rotatably provided in the distal end member;
a tool rotation drive source for rotating the tool;
an attitude altering drive source for operating the attitude of the distal end member; and
a drive unit housing to which a base end of the spindle guide section is connected,
in which the distal end member rotatably supports a spindle for holding the tool,
in which the spindle guide section has its interior accommodating a rotary shaft for transmitting a rotation of the tool rotation drive source to the spindle and a guide hole having its opposite ends opening,
in which a flexible attitude altering member is reciprocally movably inserted within the guide hole, and has a tip for undergoing a reciprocating or retracting motion in contact with the distal end member so as to alter the attitude of the distal end member, the attitude altering member being selectively advanced or retracted by the attitude altering drive source; and
further comprising a position detector for detecting an advanced or retracted position of the attitude altering member from a site separate from the attitude altering drive source.

2. The remote controlled actuator as claimed in claim 1, in which the position detector detects the advanced or retracted position of the attitude altering member from a displacement of the attitude altering member or a force transmitting member between the attitude altering drive source and the attitude altering member.

3. The remote controlled actuator as claimed in claim 2, further comprising a force increasing and transmitting mechanism provided within the drive unit housing and comprised of a lever mechanism for increasing and transmitting an output of a direct acting member, which is selectively advanced or retracted by the attitude altering drive source in a linear direction, to the attitude altering member, and
in which the position detector comprises a displacement amount measuring unit for measuring the amount of displacement of a lever of the force increasing and transmitting mechanism, which is the transmitting member, and a displacement amount estimator for estimating the advanced or retracted position of the attitude altering member from a measured value of the displacement amount measuring unit.

4. The remote controlled actuator as claimed in claim 3, in which the displacement amount measuring unit includes a to-be-detected portion, provided in the lever of the force increasing and transmitting mechanism, and a detecting portion fixed in position to the drive unit housing for detecting a displacement of the to-be-detected portion.

5. The remote controlled actuator as claimed in claim 3, in which the displacement amount measuring unit is an angle sensor for detecting the angle of rotation of the lever of the force increasing and transmitting mechanism.

6. The remote controlled actuator as claimed in claim 2, in which the position detector comprises an advanced or retracted position measuring unit for measuring the advanced or retracted position of one end of the attitude altering member adjacent the drive unit housing, and an advanced or retracted position estimator for estimating the advanced or retracted position of the attitude altering member from a measured value of the advanced or retracted position measuring unit.

7. The remote controlled actuator as claimed in claim 6, in which the advanced or retracted position measuring unit includes a to-be-detected portion provided at one end of the attitude altering member adjacent the drive unit housing and made up of a flat face lying perpendicular to a lengthwise direction of the attitude altering member, and a detecting portion fixed in position to the drive unit housing for detecting a displacement of the to-be-detected portion.

8. The remote controlled actuator as claimed in claim 6, in which the advanced or retracted position measuring unit includes a to-be-detected portion in the form of a linear encoder provided at one end of the attitude altering member adjacent the drive unit housing and having scale grids to be detected lined up on a lengthwise direction of the attitude altering member, and a detecting portion fixed in position to the drive unit housing for reading the scale grids of the to-be-detected portion.

9. The remote controlled actuator as claimed in claim 1, in which the attitude altering drive source is a rotary actuator provided outside the drive unit housing, and
further comprising a rotation/advance or retraction converting and transmitting mechanism accommodated within the drive unit housing and operable to convert the rotation of the attitude altering drive source into the advancing or retracting motion in the linear direction and then to transmit it to the attitude altering member.

10. The remote controlled actuator as claimed in claim 1, further comprising:
an activation amount measuring unit for measuring the amount of activation of the attitude altering drive source; and
an applied force estimator for estimating the magnitude of a force, which the attitude altering member applies to the distal end member, from a difference between the advanced or retracted position of the attitude altering member, that is estimated from the amount of activation of the attitude altering drive source measured by the activation amount measuring unit, and the advanced or retracted position of the attitude altering member estimated from the position detector.

11. The remote controlled actuator as claimed in claim 1, in which the spindle guide section has a curved portion.

* * * * *